(12) United States Patent
Mercep et al.

(10) Patent No.: US 7,550,498 B2
(45) Date of Patent: Jun. 23, 2009

(54) 1,2-DIAZA-DIBENZOAZULENES AS INHIBITORS OF TUMOUR NECROSIS FACTOR PRODUCTION AND INTERMEDIATES FOR THE PREPARATION THEREOF

(75) Inventors: Mladen Mercep, Zagreb (HR); Milan Mesic, Zagreb (HR); Dijana Pesic, Sibenik (HR)

(73) Assignee: GlaxoSmithKline Istrazivacki Centar Zagreb d.o.o. (HR)

( * ) Notice: Subject to any disclaimer, the term of this patent is extended or adjusted under 35 U.S.C. 154(b) by 584 days.

(21) Appl. No.: 10/515,709

(22) PCT Filed: May 20, 2003

(86) PCT No.: PCT/HR03/00022

§ 371 (c)(1),
(2), (4) Date: May 24, 2005

(87) PCT Pub. No.: WO03/099822

PCT Pub. Date: Dec. 4, 2003

(65) Prior Publication Data

US 2005/0209296 A1    Sep. 22, 2005

(30) Foreign Application Priority Data

May 23, 2002    (HR) .......................... P 20020452 A

(51) Int. Cl.
   *A61K 31/695*    (2006.01)
   *C07D 491/02*    (2006.01)
(52) U.S. Cl. ..................... 514/406; 548/358.5
(58) Field of Classification Search ............... None
See application file for complete search history.

(56) References Cited

U.S. PATENT DOCUMENTS

| | | | |
|---|---|---|---|
| 3,711,489 A | 1/1973 | Lombardino | |
| 3,773,940 A | 11/1973 | Schindler et al. | |
| 3,781,294 A | 12/1973 | Lombardino | |
| 3,859,439 A | 1/1975 | Blattner and Schindler | |
| 4,112,110 A | 9/1978 | Blattner | |
| 4,198,421 A | 4/1980 | Cherkofsky et al. | |
| 4,267,184 A | 5/1981 | Cherkofsky et al. | |
| 4,267,190 A | 5/1981 | Cherkofsky et al. | |
| 4,271,179 A | 6/1981 | van der Burg | |
| 7,312,203 B2 | 12/2007 | Mercep et al. | |
| 7,435,834 B2* | 10/2008 | Mercep et al. | ................. 549/42 |
| 2005/0148578 A1 | 7/2005 | Mercep et al. | |

FOREIGN PATENT DOCUMENTS

| | | |
|---|---|---|
| CA | 967573 | 5/1975 |
| EP | 0063525 | 10/1982 |
| EP | 0125484 | 11/1984 |
| EP | 0357126 | 3/1990 |
| EP | 0 372 445 | 6/1990 |
| HR | 20000310 | 2/2002 |
| WO | WO-91/18885 | 12/1991 |
| WO | WO 98/54186 | 12/1998 |
| WO | WO-01/87890 | 11/2001 |
| WO | WO 03/097648 | 11/2003 |

OTHER PUBLICATIONS

Olivera et al., Dibenzoxepino '4,5-d pyrazoles: a facile approach via the Ullman-ether reaction, Tetrahedron Letters, 2000, 41(22):4353-4360.
Kawashima and Kawano, Synthesis of Dibenzo-cycloprop-diazepine derivatives, J. Takeda Res. Lab, 1978, 37(1/2): 6-11.
Gansser et al., Determination de l'activite radioprotectrice d'analogues de l'imipramine, Ann. Pharmaceutique francaises, 1984, 41(5):465-471.
Fishou et al., Regioselective de la Cycloaddition Dipolaire-1,3, Tetrahedron, 1984, 40:5121-5133.
Elliott et al., Randomised double-blind comparison of chimeric monoclonal antibody to tumor necrosis factor alpha (cA2) versus placebo in rheumatoid arthritis, The Lancet, 1994, 344:1105-1110.
Pfeffer et al., Mice Deficient for the 55kd Tumor Necrosis Factor Receptor Are Resistant to Endotixic Shock, yet Succumb to L. monocytogenes Infection, Cell, 1993, 73:457-467.
Keffer at al., Transgenic mice expressing human tumour necrosis factor: a predictive genetic model of arthritis, EMBO J., 1991, 10:4025-4031.
Dinarello, Interleukin-1, Rev. Infect Disease, 1984, 6(1):51-95.
Bresnihan, Treatment with Recombinant Human Interleukin-1 Receptor Antagonist (rhIL-1ra) in Rheumatoid Arthritis (RA); Results of a Randomized Double-Blind, Placebo-Controlled Multicenter trial, Arthrit. Rheum., 1996, 39:73.
Menozzi, J. Heterocyclic Chem., 1997, 34:963-698.
Badger et al., Pharmacological Profile of SB 203580, a Selective Inhibitor of Cytokine Suppressive Binding Protein/p38 Kinase, in Animal Models of Arthritis, Bone Resorption, Endotoxin Shock and Immune Function, J. Pharmac. Env. Therap., 1996, 279(3):1453-1461.
Fukawa et al., A Method for Evaluating Analgesic Agents in Rats, J. Pharmacol. Meth., 1980, 4:251-259.
Schweizer et al., Combined automated writhing/motility test for testing analgesics, Agents and Actions, 1988, 23:29-31.
Collier et al., The Abdominal Constriction Response and Its Suppression By Analgesic Drugs in the Mouse, Br. J. Pharmac. Chemother., 1968, 32:295-310.
Dinarello, An Update on Human Interleukin-1: From Molecular Biology to Clinical Relevance, J. Clinical Immunology, 1985, 5:287.
Van Assche and Rutgeerts, Anti-TNF agents in Crohn's disease, Exp. Opin. Invest. Drugs, 2000, 9:103-111.

(Continued)

*Primary Examiner*—Kamal A Saeed
(74) *Attorney, Agent, or Firm*—J. Scott Young

(57) ABSTRACT

The present invention relates to derivatives of 1,2-diaza-dibenzoazulene, to their pharmacologically acceptable salts and solvates, to processes and intermediates for the preparation thereof as well as to their antiinflammatory actions, especially to the inhibition of tumor necrosis factor-α (TNF-α) production and the inhibition of interleukin-1 (IL-1) production as well as to their analgetic action.

11 Claims, No Drawings

OTHER PUBLICATIONS

Georgopoulos et al., Transmembrane TNF Is Sufficient To Induce Localized Tissue Toxicity and Chronic Inflammatory Arthritis In Transgenic Mice, J. Inflamm., 1996, 46:86-97.

Mori et al., Attenuation of Collagen-Induced Arthritis in 55-kDa TNF Receptor Type 1 (TNFR1)-IgG1-Treated and TNFR1-Deficient Mice, J. Immunol., 1996, 157:3178-3182.

Carswell et al., An endotoxin-induced serum factor that causes necrosis of tumors, Proc. Natl. Acad. Sci. U.S.A., 1975, 72:3666-3670.

Bennett et al. "Reaction of 5-acetyl-10, didehydro-5H-dibenz[b,f]azepine with pyrrole, N-methylpyrrole, imada and n-methylimidazole: cycloaddition versus Michael addition." J. Heterocycl. Chem., 1994, 31:293-296.

Bresnihan, "Treatment with recombinant human interleukin-1 receptor antagonist (rhIL-lra) in rheumatoid arthritis (RA); results of randomized double-blind, placebo-controlled multicenter trial," Arthrit. Rheum., 1996, 39:73.

Funke et al. Physico-chemical properties and stability of trans-5-chloro-2methyl-2,3,3a,12b-tetrahydro-1-dibenz[2,3:6,7]oxepino[4,5-c]pyrrolidine Maleate, Arzeim-Forsch., 1190, 40:536-539.

Mattioli and Ghia. "Omega-dialkylaminoalkyl ethers of phenyl-(5-substituted 1-phenyl-1H-pyrazol-4-yl)methanols with analgesic and anti-inflammatory activity." J. Heterocyclic Chem., 1997, 34:963-968.

Novacek et al. "Reaction of 8-chloro-10-phenylhydrazono-10,11-dihydro-dibenzo[b,f]thepine with aromatic aldehydes," Collection Czechoslov. Chem. Commun., 1976, vol. 41, 785-787.

Schulz et al. "Synthese von 1,3a,3,12b-tetrahydro-dibenzo[b,f]-pyrazolo[3,4-d]azepin-Derivaten." Z. Chem. 1988, 28:181-182.

Wermuth et al. "Molecular Variations Based on Isosteric Replacements," Practice of Medicinal Chemistry, 1996, pp. 203-237.

* cited by examiner

1,2-DIAZA-DIBENZOAZULENES AS INHIBITORS OF TUMOUR NECROSIS FACTOR PRODUCTION AND INTERMEDIATES FOR THE PREPARATION THEREOF

This application is a National Stage under 35 U.S.C. §371 of PCT International Application No. PCT/HR03/00022, filed May 20, 2003, which claims the benefit under 35 U.S.C. §119(e) of prior Croatian Application No. P20020452A, filed May 23, 2002, the entire contents of which are incorporated herein by reference.

TECHNICAL FIELD

The present invention relates to 1,2-diaza-dibenzoazulene derivatives, to their pharmacologically acceptable salts and solvates, to processes and intermediates for the preparation thereof as well as to their antiinflammatory effects, especially to the inhibition of tumour necrosis factor-α(TNF-α) production and the inhibition of interleukin-1 (IL-1) production as well as to their analgetic action.

PRIOR ART

There are numerous literature data relating to various 1,2- and 1,3-diaza-dibenzoazulenes and to the preparation thereof. It is well-known that some compounds of such structure and salts thereof have an antiinflammatory action and represent a novel class of compounds having such an action. Dibenzoazulenes of imidazole class with various 2-substituents such as trifluoromethyl, pyridinyl, naphthyl, phenyl and substituted phenyl, which possess an antianflammatory action, are disclosed in a series of patents (U.S. Pat. Nos. 3,711,489, 3,781,294 and CA 967,573). The corresponding imidazoles with 2-alkylthio substituents in 2-position also possess a similar action (U.S. Pat. No. 4,198,421; EP 372,445 and WO 9,118,885).

There are also known 2-substituted dibenzoazulenes of tetrahydro pyrazole class with substituents such as acyl, alkyloxycarbonyl, phenyl or substituted phenyls (Gansser C. et al., Ann. Pharm. 1984, 41: 465-471; or Olivera R et al., Tetrahedron Lett., 2000, 41:4353-4356 and 4357-4360). Some examples of 2-substituted dibenzoazulenes of pyrazole class are disclosed as well. The only such substituents known from the literature are alkyls (Kawashiha K. Takeda Kenkyusho Ho 1978, 37: 6-11, Fishou D. et al., Tetrahedron, 1984, 40: 5121-5133), phenyls or substituted phenyls (FR 2,504, 140).

Further there are known derivatives of 1-thia-dibenzoazulenes having aminoalkyloxy substituents on the thiophene ring, which possess an antiinflammatory action (WO 01/87890).

According to our knowledge and to available literature data, aromatic dibenzoazulenes of pyrazole class with hydroxyalkyl, alkyloxy or aminoalkyloxy substituents on the pyrazole ring have not been prepared or disclosed so far. It is not known either that such compounds could possess an antiinflammatory action (inhibitors of TNF-α and IL-1 secretion) or analgetic action, which is an object of the present invention.

In 1975 TNF-α was defined as a serum factor induced by endotoxin and causing tumour necrosis in vitro and in vivo (Carswell E A et al., Proc. Natl. Acad. Sci. U.S.A., 1975, 72:3666-3670). Besides antitumour action, TNF-α also possesses numerous other biological actions important in the homeostasis of organisms and in pathophysiological conditions. The main sources of TNF-α are monocytes-macrophages, T-lymphocytes and mastocytes.

The discovery that anti-TNF-α antibodies (cA2) have an action in treating patients with rheumatoid arthritis (RA) (Elliott M et al., Lancet, 1994, 344:1105-1110) led to an increased interest in finding novel TNF-α inhibitors as possible potent drugs for RA. Rheumatoid arthritis is an autoimmune chronic inflammatory disease characterized by irreversible pathological changes in the joints. In addition to RA theraphy, TNF-α antagonists may also be used in numerous pathological conditions and diseases such as spondylitis, osteoarthritis, gout and other arthritic conditions, sepsis, septic shock, toxic shock syndrom, atopic dermatitis, contact dermatitis, psoriasis, glomerulonephritis, lupus erythematosus, scleroderma, asthma, cachexia, chronic obstructive lung disease, congestive cardiac arrest, insulin resistance, lung fibrosis, multiple sclerosis, Crohn's disease, ulcerative colitis, viral infections and AIDS.

Some of the proofs indicating the biological importance of TNF-α were obtained by in vivo experiments in mice, in which mice gens for TNF-α or its receptor were inactivated. Such animals are resistant to collagen-induced arthritis (Mori L et al., J. Immunol., 1996, 157:3178-3182) and to endotoxin-caused shock (Pfeffer K et al., Cell, 1993, 73:457-467). In animal assays where TNF-α level was increased, a chronic inflammatory polyarthritis occured (Georgopoulos S et al., J. Inflamm., 1996, 46:86-97; Keffer J et al., EMBO J., 1991, 10:4025-4031) and its pathological picture was alleviated by inhibitors of TNF-α production. The treatment of such inflammatory and pathological conditions usually includes the application of non-steroid antiinflammatory drugs and, in more severe cases, gold salts, D-penicillinamine or methotrexate are administered. Said drugs act symptomatically, but they do not stop the pathological process. Novel approaches in the therapy of rheumatoid arthritis are based upon drugs such as tenidap, leflunomide, cyclosporin, FK-506 and upon biomolecules neutralizing the TNF-α action. At present there are commercially available etanercept (Enbrel, Immunex/ Wyeth), a fusion protein of the soluble TNF receptor, and infliximab (Remicade, Centocor), a chimeric monoclonal human and mouse antibody. Besides in RA therapy, etanercept and infliximab are also registered for the therapy of Crohn's disease (Exp. Opin. Invest. Drugs, 2000, 9:103).

In optimum RA therapy, besides inhibition of TNF-α secretion, also the inhibition of IL-1 secretion is very important since IL-1 is an important cytokin in cell regulation and immunoregulation as well as in pathophysiological conditions such as inflammation (Dinarello C A et al., Rev. Infect. Disease, 1984, 6:51). Well-known biological activities of IL-1 are: activation of T-cells, induction of elevated temperature, stimulation of secretion of prostaglandine or collagenase, chemotaxia of neutrophils and reduction of iron level in plasma (Dinarello C A, J. Clinical Immunology, 1985, 5:287). Two receptors to which IL-1 may bind are well-known: IL-1RI and IL-1RII. IL-1RI transfers a signal intracellularly, whereas IL-1RII, though situated on the cell surface, does not transfer a signal inside the cell. Since IL1-RII binds IL-1 as well as IL1-RI, it may act as a negative regulator of IL-1 action. Besides this mechanism of signal transfer regulation, another natural antagonist of IL-1 receptor, IL-1ra, is present in cells. This protein binds to IL-1RI, but does not bring about a stimulation thereof. The potency of IL-1ra in stopping the signal transfer is not high and its concentration has to be 500 times higher than that of IL-1 in order to achieve a break in the signal transfer. Recombinant human IL-1ra (Amgen) was clinically tested (Bresnihan B et al., Arthrit. Rheum., 1996, 39:73) and the obtained results indicated an improvement of the clinical picture in RA patients over a placebo. These results indicate the importance of the inhibition of IL-1 action in treating diseases such as RA where IL-1 production is disturbed. Since there exists a synergistic action of TNF-α and IL-1, dual TNF-α and IL-1 inhibitors may be used in treating conditions and diseases related to an enhanced secretion of TNF-α and IL-1.

Inventive Solution

The present invention relates to compounds 1,2-diazadibenzoazulenes of the formula I:

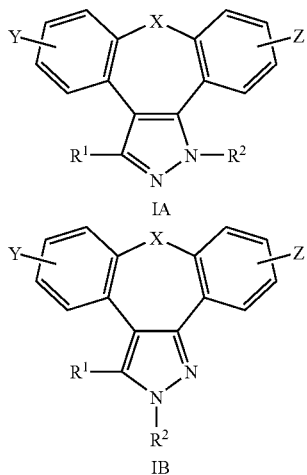

wherein

X may be $CH_2$ or a hetero atom such as O, S, S(=O), S (=O)$_2$, or $NR^a$, wherein $R^a$ is hydrogen or a protecting group;

Y and Z independently from each other denote one or more identical or different substituents linked to any available carbon atom, and may be halogen, $C_1$-$C_4$ alkyl, $C_2$-$C_4$ alkenyl, $C_2$-$C_4$ alkinyl, halo-$C_1$-$C_4$ alkyl, hydroxy, $C_1$-$C_4$ alkoxy, trifluoromethoxy, $C_1$-$C_4$ alkanoyl, amino, amino-$C_1$-$C_4$ alkyl, N—($C_1$-$C_4$ alkyl)amino, N,N-di($C_1$-$C_4$ alkyl) amino, thiol, $C_1$-$C_4$ alkylthio, sulfonyl, $C_1$-$C_4$ alkylsulfonyl, sulfinyl, $C_1$-$C_4$ alkylsulfinyl, carboxy, $C_1$-$C_4$ alkoxycarbonyl, cyano, nitro;

$R^1$ may be halogen, an optionally substituted heteroaryl or heterocycle, hydroxy, $C_1$-$C_7$ alkoxy, aryloxy, amino, N—($C_1$-$C_7$ alkyl)amino, N,N-di($C_1$-$C_7$-alkyl)amino, ($C_1$-$C_7$ alkyl)amino, amino-$C_1$-$C_7$ alkoxy, $C_1$-$C_7$ alkanoyl, aroyl, $C_1$-$C_7$ alkanoyloxy, carboxy, an optionally substituted $C_1$-$C_7$ alkyloxycarbonyl or aryloxycarbonyl, carbamoyl, N—($C_1$-$C_7$-alkyl)carbamoyl, N,N-di($C_1$-$C_7$-alkyl)carbamoyl, cyano, nitro, or a substituent of the formula II

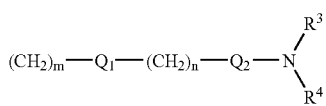

wherein $R^3$ and $R^4$ simultaneously or independently from each other may be hydrogen, $C_1$-$C_4$-alkyl, aryl or together with N have the meaning of an optionally substituted heterocycle or heteroaryl;

m and n represent an integer from 0 to 3;

$Q_1$ and $Q_2$ represent, independently from each other, oxygen, sulfur or groups:

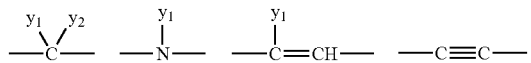

wherein the substituents $y_1$ and $Y_2$ independently from each other may be hydrogen, halogen, an optionally substituted $C_1$-$C_4$ alkyl or aryl, hydroxy, $C_1$-$C_4$ alkoxy, $C_1$-$C_4$ alkanoyl, thiol, $C_1$-$C_4$ alkylthio, sulfonyl, $C_1$-$C_4$ alkylsulfonyl, sulfinyl, $C_1$-$C_4$ alkylsulfinyl, cyano, nitro or together form carbonyl or imino group;

$R^2$ has the meaning of hydrogen, optionally substituted $C_1$-$C_7$ alkyl or aryl or a protecting group: formyl, $C_1$-$C_7$ alkanoyl, $C_0$-$C_7$ alkoxycarbonyl, arylalkyloxycarbonyl, aroyl, arylalkyl, $C_1$-$C_7$ alkylsilyl;

as well as to pharmacologically acceptable salts and solvates thereof.

The term "halo", "hal" or "halogen" relates to a halogen atom which may be fluorine, chlorine, bromine or iodine.

The term "alkyl" relates to alkyl groups with the meaning of alkanes wherefrom radicals are derived, which radicals may be straight, branched or cyclic or a combination of straight and cyclic ones and branched and cyclic ones. The preferred straight or branched alkyls are e.g. methyl, ethyl, propyl, iso-propyl, butyl, sec-butyl and tert-butyl. The preferred cyclic alkyls are e.g. cyclopentyl or cyclohexyl.

The term "haloalkyl" relates to alkyl groups which must be substituted with at least one halogen atom. The most frequent haloalkyls are e.g. chloromethyl, dichloromethyl, trifluoromethyl or 1,2-dichloropropyl.

The term "alkenyl" relates to alkenyl groups having the meaning of hydrocarbon radicals, which may be straight, branched or cyclic or are a combination of straight and cyclic ones or branched and cyclic ones, but having at least one carbon-carbon double bond. The most frequent alkenyls are ethenyl, propenyl, butenyl or cyclohexenyl.

The term "alkinyl" relates to alkinyl groups having the meaning of hydrocarbon radicals, which are straight or branched and contain at least one and at most two carbon-carbon triple bonds. The most frequent alkinyls are e.g. ethinyl, propinyl or butinyl.

The term "alkoxy" relates to straight or branched chains of alkoxy group. Examples of such groups are methoxy, propoxy, prop-2-oxy, butoxy, but-2-oxy or methylprop-2-oxy.

The term "aryl" relates to groups having the meaning of an aromatic ring, e.g. phenyl, as well as to fused aromatic rings. Aryl contains one ring with at least 6 carbon atoms or two rings with totally 10 carbon atoms and with alternating double (resonant) bonds between carbon atoms. The most freqently used aryls are e.g. phenyl or naphthyl. In general, aryl groups may be linked to the rest of the molecule by any available carbon atom via a direct bond or via a $C_1$-$C_4$ alkylene group such as methylene or ethylene.

The term "heteroaryl" relates to groups having the meaning of aromatic and partially aromatic groups of a monocyclic or bicyclic ring with 4 to 12 atoms, at least one of them being a hetero atom such as O, S or N, and the available nitrogen atom or carbon atom is the binding site of the group to the rest of the molecule either via a direct bond or via a $C_1$-$C_4$ alkylene group defined earlier. Examples of this type are thiophenyl, pyrrolyl, imidazolyl, pyridinyl, oxazolyl, thiazolyl, pyrazolyl, tetrazolyl, pirimidinyl, pyrazinyl, quinolinyl or triazinyl.

The term "heterocycle" relates to five-member or six-member, completely saturated or partly unsaturated heterocyclic groups containing at least one hetero atom such as O, S or N, and the available nitrogen atom or carbon atom is the binding site of the group to the rest of the molecule either via a direct bond or via a $C_1$-$C_4$ alkylene group defined earlier. The most frequent examples are morpholinyl, piperidinyl, piperazinyl, pyrrolidinyl, pirazinyl or imidazolyl.

The term "alkanoyl" group relates to straight chains of acyl group such as formyl, acetyl or propanoyl.

The term "aroyl" group relates to aromatic acyl groups such as benzoyl.

The term "optionally substituted alkyl" relates to alkyl groups which may be optionally additionally substituted with one, two, three or more substituents. Such substituents may be halogen atom (preferably chlorine or fluorine), hydroxy, $C_1$-$C_4$ alkoxy (preferably methoxy or ethoxy), thiol, $C_1$-$C_4$ alkylthio (preferably methylthio or ethylthio), amino, N—($C_1$-$C_4$)alkylamino (preferably N-methylamino or N-ethylamino), N,N-di($C_1$-$C_4$-alkyl)-amino (preferably dimethylamino or diethylamino), sulfonyl, $C_1$-$C_4$ alkylsulfonyl (preferably methylsulfonyl or ethylsulfonyl), sulfinyl, $C_1$-$C_4$ alkylsulfinyl (preferably methylsulfinyl).

The term "optionally substituted alkenyl" relates to alkenyl groups optionally additionally substituted with one, two or three halogen atoms. Such substituents may be e.g. 2-chloroethenyl, 1,2-dichloroethenyl or 2-bromo-propene-1-yl.

The term "optionally substituted aryl, heteroaryl or heterocycle" relates to aryl, heteroaryl or heterocyclic groups which may be optionally additionally substituted with one or two substituents. The substituents may be halogen (preferably chlorine or fluorine), $C_1$-$C_4$ alkyl (preferably methyl, ethyl or isopropyl), cyano, nitro, hydroxy, $C_1$-$C_4$ alkoxy (preferably methoxy or ethoxy), thiol, $C_1$-$C_4$ alkylthio (preferably methylthio or ethylthio), amino, N—($C_1$-$C_4$)alkylamino (preferably N-methylamino or N-ethylamino), N,N-di($C_1$-$C_4$-alkyl)-amino (preferably N,N-dimethylamino or N,N-diethylamino), sulfonyl, $C_1$-$C_4$ alkylsulfonyl (preferably methylsulfonyl or ethylsulfonyl), sulfinyl, $C_1$-$C_4$ alkylsulfinyl (preferably methylsulfinyl).

When X has the meaning of $NR^a$ and $R^a$ has the meaning of a protecting group, then $R^a$ relates to groups such as alkyl (preferably methyl or ethyl), alkanoyl (preferably acetyl), alkoxycarbonyl (preferably methoxycarbonyl or tert-butoxycarbonyl), arylmethoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl).

When $R^3$ and $R^4$ together with N have the meaning of heteroaryl or heterocycle, this means that such heteroaryls or heterocycles have at least one carbon atom replaced by a nitrogen atom through which the groups are linked to the rest of the molecule. Examples of such groups are morpholine-4-yl, piperidine-1-yl, pyrrolidine-1-yl, imidazole-1-yl or piperazine-1-yl.

The term "pharmaceutically suitable salts" relates to salts of the compounds of the formula I and include e.g. salts with $C_1$-$C_4$ alkylhalides (preferably methyl bromide, methyl chloride) (quaternary ammonium salts), with inorganic acids (hydrochloric, hydrobromic, phosphoric, metaphosphoric, nitric or sulfuric acids) or with organic acids (tartaric, acetic, citric, maleic, lactic, fumaric, benzoic, succinic, methane sulfonic or p-toluene sulfonic acids).

Some compounds of the formula I may form salts with organic or inorganic acids or bases and these are also included in the present invention.

Solvates (most frequently hydrates) which may be formed by compounds of the formula I or salts thereof are also an object of the present invention.

Depending upon the nature of particular substituents, the compounds of the formula I may have geometric isomers and one or more chiral centres so that there can exist enantiomers or diastereoisomers. The present invention also relates to such isomers and mixtures thereof including racemates.

The present invention also relates to all possible tautomeric forms of particular compounds of the formula I.

A further object of the present invention relates to the preparation of compounds of the formula I according to processes comprising a) for the compounds of the formula I, wherein $R^1$ has the meaning of CHO, a formulation of the compounds of the formula III

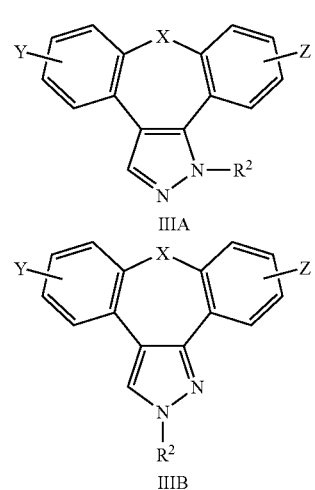

b) for the compounds of the formula I, wherein $Q_1$ has the meaning of —O—, a reaction of alcohols of the formula IV

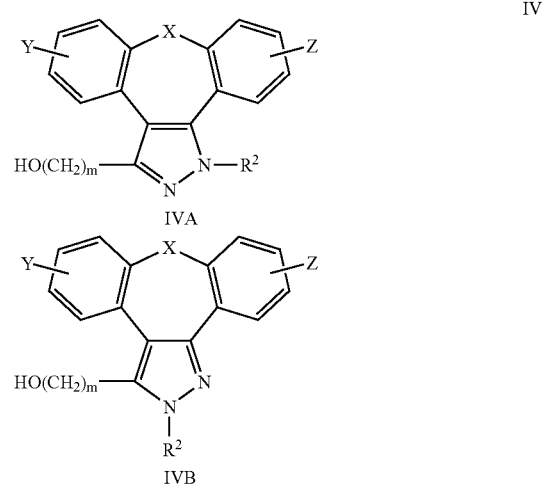

with compounds of the formula V

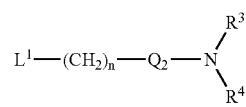

wherein $L^1$ has the meaning of a leaving group, c) for the compounds of the formula I, wherein $Q_1$ has the meaning of —O—, —NH—, —S— or —C≡C—,
a reaction of the compounds of the formula VI

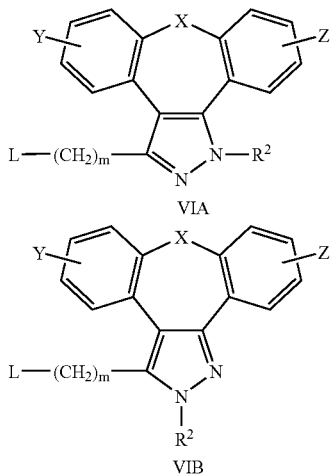

wherein L has the meaning of a leaving group, with compounds of the formula VII

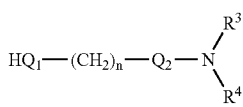

d) for the compounds of the formula I, wherein $Q_1$ has a meaning of —O—, —NH— or —S—,
a reaction of compounds of the formula VIII

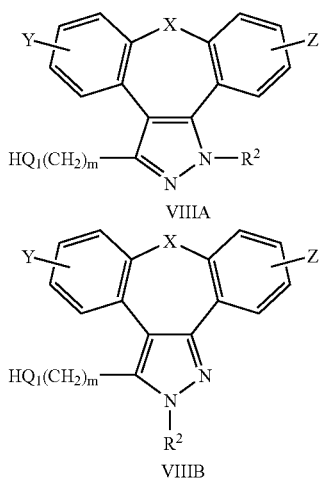

with compounds of the formula V, wherein $L^1$ has the meaning of a leaving group;
e) for the compounds of the formula I, wherein $Q_1$ has the meaning of —C≡C—, a reaction of the compounds of the formula VIII, wherein $Q_1$ has the meaning of carbonyl, with phosphorous ylides.

Preparation methods:
a) The compounds of the formula I, wherein $R^1$ has the meaning of CHO, may be obtained by formylation of the compounds of the formula III, wherein $R^2$ has the meaning of a protecting group, by the action of n-butyl-lithium at a decreased temperature (preferably −80° C.) within up to half an hour, followed by the addition of N,N-dimethylformamide and a continuation of the reaction at room temperature. The products may be isolated and purified by crystallization or chromatography on a silica gel column.

The starting substances for the preparation of the compounds of the formula III, corresponding dibenzo-azulenes of the formula IX usually consisting of tautomeric isomers IXA and IXB

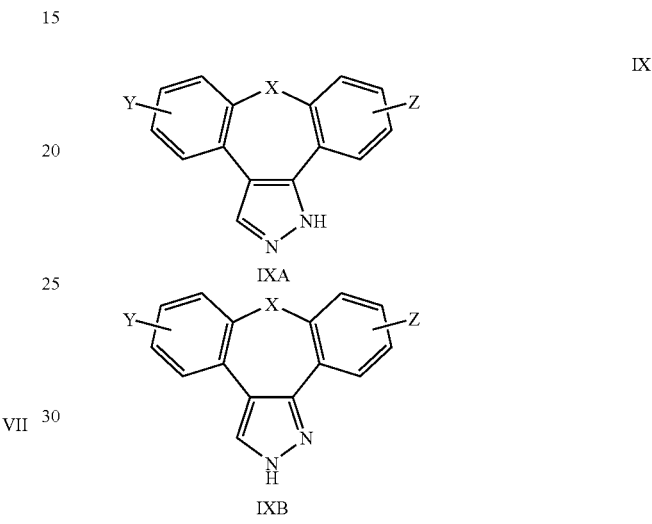

are already known or are prepared by methods disclosed for the preparation of analogous compounds. Thus, e.g. compounds of the formula III may be prepared starting from enaminoketone dibenzo-oxepine or dibenzo-thiepine, which is a product of the reaction of the corresponding ketone and dimethyl-formamide-dimethylacetal (WO 98/52937). By the reaction of optionally substituted hydrazine and enaminoketone there may be prepared 1- or 2-substituted derivatives of the formula III, whereas by the reaction of hydrazine hydrate a nonsubstituted pyrazole ring of the formula IX is formed. The free NH group of the compounds of the formula IX may be protected by the reaction with compounds of the formula X

wherein $L^2$ has the meaning of a leaving group such as halogen (most frequently chlorine or bromine), whereat the product III in the form of an isomer mixture is formed. The reaction is carried out in organic solvents such as N,N-dimethylsulfoxide, tetrahydrofuran, benzene or toluene under the addition of a strong base such as sodium hydride at an increased temperature from 50° C. to 150° C. during 1 to 5 hours. The crude product may be isolated and purified by recrystallization or chromatography on a silica gel column.

b) Compounds of the formula I according to the present process may be prepared by reaction of alcohols of the formula IV and compounds of the formula V, wherein $L^1$ has the meaning of a leaving group that may be a halogen atom (most frequently bromine, iodine or chlorine) or a sulfonyloxy group (most frequently trifluoromethylsulfonyloxy or p-toluenesulfonyloxy). The condensation reaction may be carried out according to methods disclosed for the preparation of analogous compounds (Menozzi G et al., *J. Heterocyclic Chem.*, 1997, 34:963-968 or WO 01/87890). The reaction is carried out at a temperature from 20° C. to 100° C. during 1 to 24 hours in a two-phase system (preferably with 50% NaOH/toluene) in the presence of a phase transfer catalyst (preferably benzyl triethyl ammonium chloride, benzyl triethyl ammonium bromide, cetyl trimethyl bromide). After the treatment of the reaction mixture, the products formed are isolated by recrystallization or chromatography on a silica gel column.

The starting substances, alcohols of the formula IV, may be prepared from the compounds of the formula I, wherein $R^1$ has the meaning of a suitable functional group. Thus e.g. alcohols of the formula IV may be obtained by the reduction of aldehyde, carboxyl or alkyloxycarbonyl group (e.g. methyloxycarbonyl or ethyloxycarbonyl) by using metal hydrides such as lithium aluminum hydride or sodium borohydride. Further, alcohols of the formula IV may be prepared by the hydrolysis of the corresponding esters in an alkaline or acidic medium.

The starting compounds of the formula V are already known or are prepared according to methods disclosed for the preparation of analogous compounds.

c) Compounds of the formula I according to the present process may be prepared by reacting compounds of the formula VI, wherein L has the meaning of a leaving group defined earlier for $L^1$, and compounds of the formula VII, wherein $Q_1$ has the meaning of oxygen, nitrogen, sulfur or —C≡C—. The most suitable condensation reactions are reactions of nucleophilic substitution on a saturated carbon atom as disclosed in the literature.

The starting compounds of the formula VI (most frequently halides) may be obtained by halogenation (e.g. bromination or chlorination) of compounds of the formula IV with usual halogenating agents (hydrobromic acid, $PBr_3$, $SOCl_2$ or $PCl_5$) by processes as disclosed in the literature. The obtained compounds may be isolated or may be used without isolation as suitable intermediates for the preparation of the compounds of the formula I.

The starting compounds of the formula VII are already known or are prepared according to methods disclosed for the preparation of analogous compounds.

d) The compounds of the formula I, wherein $Q_1$ has the meaning of —O—, —NH— or —S—, may be prepared by condensation of the compounds of the formula VIII and of compounds of the formula V, wherein $L^1$ has the meaning of a leaving group defined earlier. The reaction may be carried out at reaction conditions disclosed in method b) or under the conditions of reactions of nucleophilic substitution disclosed in the literature. The starting alcohols, amines and thiols may be obtained by a reaction of water, ammonia or hydrogen sulfide with compounds VI according to processes disclosed in the literature.

e) The alcohols of the structure IV may be oxidized to corresponding compounds of the formula VIII, wherein $Q_1$ has the meaning of carbonyl and which may further, by reaction with corresponding ylide reagents, result in a prolongation of the chain and in the formation of an alkenyl substituent with carbonyl or ester groups as disclosed in HR patent application No. 20000310.

Besides the above-mentioned reactions, the compounds of the formula I may be prepared by transforming other compounds of the formula I and it is to be understood that the present invention also comprises such compounds and processes. A special example of a change of a functional group is the reaction of the aldehyde group with chosen phosphorous ylides resulting in a prolongation of the chain and the formation of an alkenyl substituent with carbonyl or ester groups as disclosed in HR patent application No. 20000310. These reactions are carried out in solvents such as benzene, toluene or hexane at elevated temperature (most frequently at boiling temperature).

By reacting the compounds of the formula VI with 1-alkyne in an alkaline medium (such as sodium amide in ammonia), the compounds of the formula I, wherein $Q_1$ is —C≡C—, are obtained. The reaction conditions of this process are disclosed in the literature. At similar reaction conditions (nucleophilic substitution) various ether, thioether or amine derivatives may be prepared.

The formylation of the compounds of the formula I by processes such as e.g. Vilsmeier acylation or reaction of n-BuLi and N,N-dimethylformamide is a further general example of a transformation. The reaction conditions of these processes are well-known in the literature.

By hydrolysis of the compounds of the formula I having nitrile, amide or ester groups, there may be prepared compounds with a carboxyl group, which are suitable intermediates for the preparation of other compounds with novel functional groups such as e.g. esters, amides, halides, anhydrides, alcohols or amines.

Oxidation or reduction reactions are a further possibility of the change of substituents in the compounds of the formula I. Most frequently used oxidation agents are peroxides (hydrogen peroxide, m-chloroperbenzoic acid or benzoyl peroxide) or permanganate, chromate or perchlorate ions. Thus e.g. by the oxidation of an alcohol group by pyridinyl dichromate or pyridinyl chlorochromate, an aldehyde group is formed, which group may be converted to a carboxyl group by further oxidation. By oxidation of the compounds of the formula I, wherein $R^1$ has the meaning of alkyl, with lead tetraacetate in acetic acid or with N-bromosuccinimide using a catalytic amount of benzoyl peroxide, a corresponding carbonyl derivative is obtained.

By a selective oxidation of alkylthio group, alkylsulfinyl or alkylsulfonyl groups may be prepared.

By the reduction of the compounds with a nitro group, the preparation of amino compounds is made possible. The reaction is carried out under usual conditions of catalytic hydrogenation or electrochemically. By catalytic hydrogenation using palladium on carbon, alkenyl substituents may be converted to alkyl ones or nitrile group can be converted to aminoalkyl.

Various substituents of the aromatic structure in the compounds of the formula I may be introduced by standard substitution reactions or by usual changes of individual functional groups. Examples of such reactions are aromatic substitutions, alkylations, halogenation, hydroxylation as well as oxidation or reduction of substituents. Reagents and reaction conditions are known from the literature. Thus e.g. by aromatic substitution a nitro group is introduced in the presence of concentrated nitric acid and sulfuric acid. By using acyl halides or alkyl halides, the introduction of an acyl group or an alkyl group is made possible. The reaction is carried out in the presence of Lewis acids such as aluminum- or iron-trichloride in conditions of Friedel-Craft reaction. By the reduction of the nitro group, an amino group is obtained, which is by a diazotizing reaction converted to a suitable starting group, which may be replaced with one of the following groups: H, CN, OH, Hal.

In order to prevent undesired interaction in chemical reactions, it is often necessary to protect certain groups such as e.g. hydroxy, amino, thio or carboxy. For this purpose a great number of protecting groups may be used [Green T W, Wuts P G H, Protective Groups in Organic Synthesis, John Wiley and Sons, 1999)] and the choice, use and elimination thereof are conventional methods in chemical synthesis.

A convenient protection for amino or alkylamino groups are groups such as e.g. alkanoyl (acetyl), alkoxycarbonyl (methoxycarbonyl, ethoxycarbonyl or tert-butoxycarbonyl); arylmethoxycarbonyl (benzyloxycarbonyl), aroyl (benzoyl) or alkylsilyl (trimethylsilyl or trimethylsilylethoxymethyl) groups. The conditions of removing a protecting group depend upon the choice and the characteristics of this group. Thus e.g. acyl groups such as alkanoyl, alkoxycarbonyl or aroyl may be eliminated by hydrolysis in the presence of a base (sodium hydroxide or potassium hydroxide), tert-butoxycarbonyl or alkylsilyl (trimethylsilyl) may be eliminated by treatment with a suitable acid (hydrochloric, sulfuric, phosphoric or trifluoroacetic acid), whereas arylmethoxycarbonyl group (benzyloxycarbonyl) may be eliminated by hydrogenation using a catalyst such as palladium on carbon.

Salts of the compounds of the formula I may be prepared by generally known processes such as e.g. by reacting the compounds of the formula I with a corresponding base or acid in an appropriate solvent or solvent mixture e.g. ethers (diethylether) or alcohols (ethanol, propanol or isopropanol).

Another object of the present invention concerns the use of the present compounds in the therapy of inflammatory diseases and conditions, especially all diseases and conditions induced by excessive TNF-α and IL-1 secretion.

An effective dose of inhibitors of production of cytokins or inflammation mediators, which are the object of the present invention, or pharmacologically acceptable salts thereof may be used in the production of drugs for the treatment and prophylaxis of any pathological condition or disease induced by excessive unregulated production of cytokins or inflammation mediators.

The present invention specifically relates to an effective dose of TNF-α inhibitor, which may be determined by usual methods.

The present invention further relates to a pharmaceutical formulation containing an effective non-toxic dosis of the present compounds as well as pharmaceutically acceptable carriers or solvents.

The preparation of pharmaceutical formulations may include blending, granulating, tabletting and dissolving the ingredients. Chemical carriers may be solid or liquid. Solid carriers may be lactose, sucrose, talcum, gelatine, agar, pectin, magnesium stearate, fatty acids etc. Liquid carriers may be syrups, oils such as olive oil, sunflower oil or soya bean oil, water etc. Similarly, the carrier may also contain a component for a sustained release of the active component such as e.g. glyceryl monostearate or glyceryl distearate. Various forms of pharmaceutical formulations may be used. By the use of solid carrier there may be prepared tablets, hard gelatine capsules, powder or granules that may be administered in capsules per os. The amount of the solid carrier may vary, but it is mainly from 25 mg to 1 g. If a liquid carrier is used, the formulation would be in the form of a syrup, emulsion, soft gelatine capsules, sterile injectable liquids such as ampoules or non-aqueous liquid suspensions.

Compounds according to the present invention may be applied per os, parenterally, locally, intranasally, intrarectally and intravaginally. The parenteral route herein means intravenous, intramuscular and subcutaneous applications. Appropriate formulations of the present compounds may be used in the prophylaxis as well as in the treatment of inflammatory diseases and conditions induced by an excessive unregulated production of cytokins or inflammation mediators, primarily TNF-α. They comprise rheumatoid arthritis, rheumatoid spondylitis, osteoarthritis and other arthritic pathological conditions and diseases, eczemas, psoriasis and other inflammatory skin conditions, inflammatory eye diseases, Crohn's disease, ulcerative colitis and asthma.

The inhibitory action of the present compounds upon TNF-α and IL-1 secretion was determined by the following in vitro and in vivo experiments:

Determination of TNF-α and IL-1 Secretion in Human Peripheral Blood Mononuclear Cells in Vitro Human peripheral blood mononuclear cells (PBMC) were prepared from heparinized whole blood after separating PBMC on Ficoll-Paque™Plus (Amersham-Pharmacia). To determine the TNF-α level, $3.5-5 \times 10^4$ cells were cultivated in a total volume of 200 μl for 18 to 24 hours on microtitre plates with a flat bottom (96 wells, Falcon) in RPMI 1640 medium, into which there were added 10% of FBS (Fetal Bovine Serum, Biowhittaker) previously inactivated at 56° C./30 min, 100 units/ml of penicillin, 100 mg/ml of streptomycin and 20 mM HEPES (GIBCO). The cells were incubated at 37° C. in an atmosphere with 5% $CO_2$ and 90% humidity. In a negative control the cells were cultivated only in the medium (NC), whereas in a positive control TNF-α secretion was triggered by adding 1 ng/ml of lipopolysaccharides (LPS, *E. coli* serotype 0111:B4, SIGMA) (PC). The effect of the tested substances upon TNF-α secretion was investigated after adding them into cultures of cells stimulated by LPS (TS). The TNF-α level in the cell supernatant was determined by ELISA procedure according to the suggestions of the producer (R&D Systems). The test sensitivity was <3 pg/ml TNF-α. The IL-1 level was determined in an assay under the same conditions and with the same number of cells and the same concentration of the stimulus by ELISA procedure (R&D Systems). The percentage of inhibition of TNF-α or IL-1 production was calculated by the equation:

% inhibition=[1−(*TS−NC*)/(*PC−NC*)]*100.

The $IC_{50}$ value was defined as the substance concentration, at which 50% of TNF-α production were inhibited.

Compounds showing $IC_{50}$ with 20 μM or lower concentrations are active.

Determination of TNF-α and IL-1 Secretion in Mouse Peritoneal Macrophages in Vitro In order to obtain peritoneal macrophages, Balb/C mouse strain males, age 8 to 12 weeks, were injected i.p. with 300 μg of zymosan (SIGMA) dissolved in a phosphate buffer (PBS) in a total volume of 0.1 ml/mouse. After 24 hours the mice were euthanized according to the Laboratory Animal Welfare Act. The peritoneal cavity was washed with a sterile physiological solution (5 ml). The obtained peritoneal macrophages were washed twice with a sterile physiological solution and, after the last centrifugation (350 g/10 min), resuspended in RPMI 1640, into which 10% of FBS portion were added. In order to determine TNF-α secretion, $5 \times 10^4$ cells/well were cultivated in a total volume of 200 μl for 18 to 24 hours on microtitre plates with a flat bottom (96 wells, Falcon) in RPMI 1640 medium, into which 10% of fetal bovine serum (FBS, Biowhittaker) inactivated by heat, 100 units/ml of penicillin, 100 mg/ml of streptomycin, 20 mM HEPES and 50 μM 2-mercaptoethanol (all of GIBCO) were added. The cells were incubated at 37° C. in an atmosphere with 5% $CO_2$ and 90% humidity. In a negative control the cells were cultivated only in a medium (NC), whereas in a positive control the TNF-α secretion was triggered by adding 10 ng/ml of lipopolysaccharides (LPS, *E. coli* serotype 0111:B4, SIGMA) (PC). The effect of the substances upon the TNF-α secretion was investigated after adding them into cultures of cells stimulated with LPS (TS). The TNF-α and IL-1 levels in the cell supernatant were determined by ELISA procedure specific for TNF-α and IL-1 (R&D Systems, Biosource). The percentage of inhibition of TNF-α or IL-1 production was calculated by the equation:

% inhibition=[1−(TS−NC)/(PC−NC)]*100.

The $IC_{50}$ value was defined as the substance concentration, at which 50% of TNF-α production were inhibited.

Compounds showing $IC_{50}$ with 10 μM or lower concentrations are active.

In Vivo Model of LPS-Induced Excessive TNF-α or IL-1 Secretion in Mice

TNF-α or IL-1 secretion in mice was induced according to the already disclosed method (Badger AM et al., *J. Pharmac. Env. Therap.*, 1996, 279:1453-1461). Balb/C males, age 8 to 12 weeks, in groups of 6 to 10 animals were used. The animals were treated p.o. either with a solvent only (in negative and in positive controls) or with solutions of substances 30 minutes prior to i.p. treatment with LPS (*E. coli* serotype 0111:B4, Sigma) in a dosis of 1-25 μg/animal. Two hours later the animals were euthanized by means of i.p. Roumpun (Bayer) and Ketanest (Parke-Davis) injection. A blood sample of each animal was taken into a Vacutainer tube (Becton Dickinson) and the plasma was separated according to the producer's instructions. The TNF-α level in the plasma was determined by ELISA procedure (Biosource, R&D Systems) according to the producer's instructions. The test sensitivity was <3 pg/ml TNF-α. The IL-1 level was determined by ELISA procedure (R&D Systems). The percentage of inhibition of TNF-α or IL-1 production was calculated by the equation:

% inhibition=[1−(TS−NC)/(PC−NC)]*100.

Active are the compounds showing 30% or more inhibition of TNF-α production at a dosis of 10 mg/kg.

Writhing Assay for Analgetic Activity

In this assay pain is induced by the injection of an irritant, most frequently acetic acid, into the peritoneal cavity of mice. Animals react with characteristic writhings, which has given the name of the assay (Collier HOJ et al., *Pharmac. Chemother.*, 1968, 32:295-310; Fukawa K et al., *J. Pharmacol. Meth.*, 1980, 4:251-259; Schweizer A et al., *Agents Actions*, 1988, 23:29-31). The assay is convenient for the determination of analgetic activity of compounds. Procedure: male Balb/C mice (Charles River, Italy), age 8 to 12 weeks, were used. A control group received methyl cellulose p.o. 30 minutes prior to i.p. application of acetic acid in a concentration of 0.6%, whereas test groups received standard (acetylsalicylic acid) or test substances in methyl cellulose p.o. 30 minutes prior to i.p. application of 0.6% acetic acid (volume 0.1 ml/10 g). The mice were placed individually under glass funnels and the number of writhings was registered for 20 minutes for each animal. The percentage of writhing inhibition was calculated according to the equation:

% inhibition=(mean value of number of writhings in the control group−number of writhings in the test group)/number of writhings in the control group*100.

Active are the compounds showing such analgetic activity as acetylsalicylic acid or better.

In Vivo Model of LPS-Induced Shock in Mice

Male Balb/C mice (Charles River, Italy), age 8 to 12 weks, were used. LPS isolated from *Serratie marcessans* (Sigma, L-6136) was diluted in sterile physiological solution. The first LPS injection was administered intradermally in a dosis of 4 μg/mouse. 18 to 24 hours later, LPS was administered i.v. in a dosis of 90-200 μg/mouse. A control group received two LPS injections as disclosed above. The test groups received substances p.o. half an hour prior to each LPS application. Survival after 24 hours was observed.

Active are the substances at which the survival at a dosis of 30 mg/kg was 40% or more.

Compounds from Examples 3-9 show activity in at least two investigated assays though these results only represent an illustration of biological activity of compounds and should not limit the invention in any way.

PREPARATION PROCESSES WITH EXAMPLES

Example 1

2-(8-Oxa-1,2-diaza-dibenzo[e,h]azulene-1-yl)-ethanol (14A)

2-(8-Oxa-1,2-diaza-dibenzo[e,h]azulene-2-yl)-ethanol (14B)

An ethanolic solution of 11-dimethylaminomethylene-11H-dibenzo[b,f]oxepin-10-one (2.8 mmole in 10 ml of ethanol) was cooled to 0° C. and ethanol hydrazine (3.1 mmole) was added thereto. The reaction mixture was stirred at a temperature 0-5° C. for 2 hours. Then the solvent was evaporated and the evaporated content was extracted with ethyl acetate. The crude product was purified by chromatography on a silica gel column, whereupon an oily product was isolated.

According to the above process, starting from 11-dimethylaminomethylene-11H dibenzo[b,f]oxepin-10-one there were also isolated tautomeric isomers:
2-(8-thia-1,2-diaza-dibenzo[e,h]azulene-1-yl)-ethanol (15A) and
2-(8-thia-1,2-diaza-dibenzo[e,h]azulene-2-yl)-ethanol (15B).

Example 2

(2-Phenethyl-2H-8-oxa-1,2-diaza-dibenzo[e,h]azulene-3-yl)-methanol (16B)

To a methanolic solution of compound 9B (1.64 mmole) cooled to 0° C., $NaBH_4$ (2 mmole) was added. The reaction mixture was stirred for 2 hours at a temperature from 0 to 5° C. Then the reaction mixture was neutralized by the addition of acetic acid, the solvent was evaporated under reduced pressure and the dry residue was extracted with dichloromethane. The crude organic product (yellow oil) was dissolved in a small amount of ethyl acetate and by the addition of hexane a pure product in the form of white crystals was obtained.

According to the above process, starting from: 10B, 11B, 12B, 13B there were prepared and isolated the alcohols:
(2-phenethyl-2H-8-thia-1,2-diaza-dibenzo[e,h]azulene-3-yl)-methanol (17B),
[2-(2-trimethylsilyl-ethoxymethyl)-2H-8-oxa-1,2-diaza-dibenzo[e,h]azulene-3-yl]-methanol (18B),
[2-(2-trimethylsilyl-ethoxymethyl)-2H-8-thia-1,2-diaza-dibenzo[e,h]azulene-3-yl]-methanol (19B),
[11-chloro-2-(2-trimethylsilyl-ethoxymethyl)-2H-8-oxa-1,2-diaza-dibenzo[e,h]azulene-3-yl]-methanol (20B).

TABLE 1

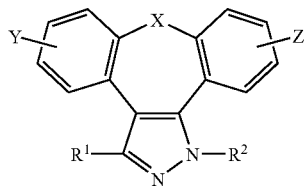

IA

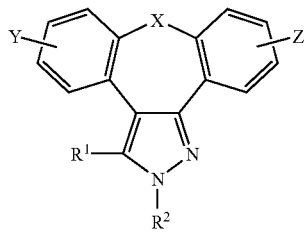

IB

| Comp. | X | Y | Z | R¹ | R² | MS | ¹H NMR(ppm) |
|---|---|---|---|---|---|---|---|
| 14A | O | H | H | H | HO(CH$_2$)$_2$ | 301.0[M + Na$^+$] | — |
| 14B | O | H | H | H | HO(CH$_2$)$_2$ | 301.0[M + Na$^+$] | — |
| 15A | S | H | H | H | HO(CH$_2$)$_2$ | 295.1[MH]$^+$ | 3.86(bs, 1H); 4.07-4.21(m, 2H); 4.36-4.44(m, 1H); 4.54-4.65(m, 1H); 7.28-7.76(m, 8H); 7.89(s, 1H) |
| 15B | S | H | H | H | HO(CH$_2$)$_2$ | 295.1[MH]$^+$ | 3.10(bs, 1H); 4.12(m, 2H); 4.45(m, 2H); 7.28-7.66(m, 7H); 7.77(s, 1H); 7.82(m, 1H) |
| 16B | O | H | H | HOCH$_2$ | Ph(CH$_2$)$_2$ | 369.4[MH]$^+$ | 3.31(t, 2H); 4.47(s, 2H); 4.56(t, 2H); 7.08-7.41(m, 12H); 7.90(d, 1H) |
| 17B | S | H | H | HOCH$_2$ | Ph(CH$_2$)$_2$ | 385[MH]$^+$ | 1.85(bs, 1H); 3.27-3.43(m, 2H); 4.32-4.57(m, 4H); 7.08-7.87(m, 13H) |
| 18B | O | H | H | HOCH$_2$ | SEM$^a$ | 395.2[MH]$^+$ | 0.03(s, 9H); 0.89-1.1(m, 2H); 2.91(bs, 1H); 3.77(t, 2H); 4.69-4.98(dd, 2H); 5.72-5.87(dd, 2H); 7.30-7.85(m, 8H) |
| 19B | S | H | H | HOCH$_2$ | SEM | 411.1[MH]$^+$ | 0.03(s, 9H); 0.85-0.99(m, 2H); 2.81(bs, 1H); 3.77(t, 2H); 4.8(dd, 2H); 5.85(m, 2H); 7.24-7.85(m, 8H) |
| 20B | O | H | 11-Cl | HOCH$_2$ | SEM | 429.2[MH]$^+$ | 0.02(s, 9H); 0.89-1.1(m, 2H); 3.69-3.77(m, 2H); 4.89(s, 2H); 5.76(s, 2H); 7.24-7.45(m, 7H) |

$^a$SEM = (CH$_3$)$_3$SiCH$_2$CH$_2$OCH$_2$

Example 3 a) Dimethyl-{2-[2-(8-thia-1,2-diaza-dibenzo[e,h]azulene-1-yl)-ethoxy]-ethyl}-amine b(IA; X=S, Y=Z=R¹=H, R²=(CH$_3$)$_2$N(CH$_2$)$_2$OCH$_2$CH$_2$)

To a solution of 2-dimethylaminoethylchloride-hydrochloride (1.1 mmole) in 50% sodium hydroxide (5 ml), benzyltriethylammonium chloride (of a catalytic amount) and a solution of alcohol 15A (0.17 mmole) in toluene (5 ml) were added. The reaction mixture was heated at boiling temperature under vigorous stirring for 4 hours. Then it was cooled to room temperature, diluted with water and extracted with dichloromethane. The organic extract was washed with water, dried over anhydrous Na$_2$SO$_4$ and evaporated under reduced pressure. After purifying the evaporation residue by chromatography on a column, an oily product was isolated.

¹H NMR (ppm, CDCl$_3$): 2.29 (s, 6H); 2.57 (m, 2H); 3.58 (m, 2H); 3.93-4.11 (m, 2H); 4.38-4.59 (m, 2H); 7.14-7.74 (m, 8H); 7.85 (s, 1H).

MS (m/z): 366 [MH]$^+$.

b) Dimethyl-{3-[2-(8-thia-1,2-diaza-dibenzo[e,h]azulene-1-yl)-ethoxy]-propyl}-amine (IA; X=S, Y=Z=R¹=H, R²=(CH$_3$)$_2$N(CH$_2$)$_3$OCH$_2$CH$_2$)

By the reaction of alcohol 15A (0.17 mmole) and 3-dimethylaminopropylchloride-hydrochloride (0.95 mmole), an oily product was obtained.

¹H NMR (ppm, CDCl$_3$): 1.8 (m, 2H); 2.34 (s, 6H); 2.47 (m, 2H); 3.45 (m, 2H); 3.91-4.03 (m, 2H); 4.39-4.52 (m, 2H); 7.29-7.74 (m, 8H); 7.86 (s, 1H).

MS(m/z): 380.1 [MH]$^+$.

Example 4 a) Dimethyl-{2-[2-(8-thia-1,2-diaza-dibenzo[e,h]azulene-2-yl)-ethoxy]-ethyl}-amine (IB; X=S, Y=Z=R¹=H, R²=(CH$_3$)$_2$N(CH$_2$)$_2$OCH$_2$CH$_2$)

To a solution of 2-dimethylaminoethylchloride-hydrochloride (2.1 mmole) in 50% sodium hydroxide (10 ml), benzyltriethylammonium chloride (20 mg) and a solution of alcohol 15B (0.34 mmole) in toluene (10 ml) were added. The reaction mixture was heated at boiling temperature under vigorous stirring for 4 hours. Then it was cooled to room temperature, diluted with water and extracted with dichloromethane.

The organic extract was washed with water, dried over anhydrous $Na_2SO_4$ and evaporated under reduced pressure. After purifying the evaporation residue by chromatography on a column, an oily product was isolated.

MS(m/z): 366.2 $[MH]^+$.

b) Dimethyl-{3-[2-(8-thia-1,2-diaza-dibenzo[e,h]azulene-2-yl)-ethoxy]-propyl}-amine (IB; X=S, Y=Z=$R^1$=H, $R^2$=$(CH_3)_2N(CH_2)_3OCH_2CH_2$)

By the reaction of alcohol 15B (0.34 mmole) and 3-dimethylaminopropylchloride-hydrochloride (1.9 mmole), an oily product was obtained.

MS(m/z): 380.2 $[MH]^+$.

Example 5 a) Dimethyl-[2-(2-phenethyl-2H-8-oxa-1,2-diaza-dibenzo[e,h]azulene-3-ylmethoxy)-ethyl]-amine (IB; X=O, Y=Z=H, $R^1$=$(CH_3)_2N(CH_2)_2OCH_2$, $R^2$=$C_6H_5CH_2CH_2$)

To a solution of 2-dimethylaminoethylchloride-hydrochloride (5.2 mmole) in 50% sodium hydroxide (5 ml), benzyltriethylammonium chloride (50 mg) and a solution of alcohol 16B (0.41 mmole) in toluene (15 ml) were added. The reaction mixture was heated at boiling temperature under vigorous stirring for 3 hours. Then it was cooled to room temperature, diluted with water and extracted with dichloromethane. The organic extract was washed with water, dried over anhydrous $Na_2SO_4$ and evaporated under reduced pressure. After purifying the evaporation residue by chromatography on a column, an oily product was isolated.

$^1$H NMR (ppm, $CDCl_3$): 2.28 (m, 6H); 2.56 (m, 2H); 3.28 (t, 2H); 3.61 (t, 2H); 4.37 (s, 2H); 4.52 (t, 2H); 7.15-7.85 (m, 13H).

MS(m/z): 440.4 $[MH]^+$.

b) Dimethyl-[3-(2-phenethyl-2H-8-oxa-1,2-diaza-dibenzo[e,h]azulene-3-ylmethoxy)-propyl]-amine (IB; X=O, Y=Z=H, $R^1$=$(CH_3)_2N(CH_2)_3OCH_2$, $R^2$=$C_6H_5CH_2CH_2$)

By the reaction of alcohol 16B (0.41 mmole) and 3-dimethylaminopropylchloride-hydrochloride (5.1 mmole), an oily product was obtained.

$^1$H NMR (ppm, $CDCl_3$): 2.04 (m, 2H); 2.55 (s, 6H); 2.78 (m, 2H); 2.92 (m, 2H); 3.57 (t, 2H); 4.32 (s, 2H); 4.51 (t, 2H); 7.13-7.86 (m, 13H).

MS(m/z): 454.4 $[MH]^+$.

Example 6 a) Dimethyl-[2-(2-phenethyl-2H-8-thia-1,2-diaza-dibenzo[e,h]azulene-3-ylmethoxy)-ethyl]-amine (IB; X=S, Y=Z=H, $R^1$=$(CH_3)_2N(CH_2)_2OCH2$, R=$C_6H_5CH_2CH_2$)

To a solution of 2-dimethylaminoethylchloride-hydrochloride (5.2 mmole) in 50% sodium hydroxide (5 ml), benzyltriethylammonium chloride (50 mg) and a solution of alcohol 17B (3.3 mmole) in toluene (15 ml) were added. The reaction mixture was heated at boiling temperature under vigorous stirring for 4 hours. Then it was cooled to room temperature, diluted with water and extracted with dichloromethane. The organic extract was washed with water, dried over anhydrous $Na_2SO_4$ and evaporated under reduced pressure. After purifying the evaporation residue by chromatography on a column, an oily product was isolated.

$^1$H NMR (ppm, $CDCl_3$): 2.72 (d, 6H); 3.08 (m, 2H); 3.32 (m, 2H); 3.86 (m, 2H); 4.15-4.27 (m, 2H); 4.58 (m, 2H); 7.11-7.84 (m, 13H).

MS(m/z): 456.1 $[MH]^+$.

b) Dimethyl-[3-(2-phenethyl-2H-8-thia-1,2-diaza-dibenzo [e,h]azulene-3-ylmethoxy)-propyl]-amine (IB, X=S, Y=Z=H, $R^1$=$(CH_3)_2N(CH_2)_3OCH_2$, R=$C_6H_5CH_2CH_2$)

By the reaction of alcohol 17B (0.33 mmole) and 3-dimethylaminopropylchloride-hydrochloride (5.1 mmole), an oily product was obtained.

$^1$H NMR (ppm, $CDCl_3$): 1.96 (m,2H); 2.44 (s, 6H); 2.65 (m,2H); 2.83 (m, 2H); 3.32 (m,1H); 3.55 (m, 1H); 3.89 (m, 2H); 4.2-4.55 (m, 2H); 7.1-7.8 (m, 13H).

MS(m/z): 470.1 $[MH]^+$.

Example 7 a) Dimethyl-{2-[2-(2-trimethylsilyl-ethoxymethyl)-2H-8-oxa-1,2-diaza-dibenzo[e,h]azulene-3-yl-methoxy]-ethyl}-amine (IB; X=O, Y=Z=H, $R^1$= $(CH_3)_2N(CH_2)_2OCH_2$, $R^2$=$(CH_3)_3Si(CH_2)_2OCH_2$)

Dimethyl-[2-(1H-8-oxa-1,2-diaza-dibenzo[e,h]azulene-3-ylmethoxy)-ethyl]-amine (IA; X=O, Y=Z=$R^1$=$(CH_3)_2OCH_2$, $R^2$=H)

Dimethyl-[2-(2H-8-oxa-1,2-diaza-dibenzo[e,h]azulene-3-ylmethoxy)-ethyl]-amine (IB; X=O, Y=Z=$R^1$=$(CH_3)_2N(CH_2)_2OCH_2$, $R^2$=H)

To a solution of 2-dimethylaminoethylchloride-hydrochloride (2.43 mmole) in 50% sodium hydroxide (5 ml), benzyltriethylammonium chloride (a catalytic amount) and a solution of alcohol 18B (0.35 mmole) in toluene (5 ml) were added. The reaction mixture was heated under vigorous stirring and reflux for 4 hours. Then it was cooled to room temperature, diluted with water and extracted with dichloromethane. The organic extract was washed with water, dried over anhydrous $Na_2SO_4$ and evaporated under reduced pressure. The obtained product dimethyl-{2-[2-(2-trimethylsilyl-ethoxymethyl)-2H-8-oxa-1,2-diaza-dibenzo[e,h]azulene-3-ylmethoxy]-ethyl}-amine in an oily form was used in a further synthesis without additional purification.

In 0.5M HCl in methanol (4 ml), dimethyl-{2-[2-(2-trimethylsilyl-ethoxymethyl)-2H-8-oxa-1,2-diaza-dibenzo[e,h]azulene-3-ylmethoxy]-ethyl}-amine was dissolved and the reaction mixture was heated at boiling temperature for 4 hours. Then the reaction mixture was neutralized by the addition of a saturated sodium hydrogencarbonate solution and the organic product was extracted with dichloromethane. The crude product was purified by chromatography on a silica gel column, whereupon an oily product, a tautomeric mixture of dimethyl-[2-(1H-8-oxa-1,2-diaza-dibenzo[e,h]azulene-3-ylmethoxy)-ethyl]-amine and dimethyl-[2-(2H-8-oxa-1,2-diaza-dibenzo[e,h]azulene-3-ylmethoxy)-ethyl]-amine in the form of an oil was isolated.

MS (m/z): 336 $[MH]^+$; 335 $[M-H]^-$.

b) Dimethyl-{3-[2-(2-trimethylsilyl-ethoxymethyl)-2H-8-oxa-1,2-diaza-dibenzo[e,h]azulene-3-yl-methoxy]-propyl}-amine (IB; X=O, Y=Z=H, R$^1$=(CH$_3$)$_2$N(CH$_2$)$_3$OCH$_2$R$^2$=(CH$_3$)$_3$Si(CH$_2$)$_2$OCH$_2$ Dimethyl-[3-(1H-8-oxa-1,2-diaza-dibenzo[e,h]azulene-3-ylmethoxy)-propyl]-amine (IA; X=O, Y=Z=H, R$^1$=(CH$_3$)$_2$N(CH$_2$)$_3$OCH$_2$, R$^2$=H)

Dimethyl-[3-(2H-8-oxa-1,2-diaza-dibenzo[e,h]azulene-3-ylmethoxy)-propyl]-amine (IB; X=O, Y=Z=H, R$^1$=(CH$_3$)$_2$N(CH$_2$)$_3$OCH$_2$, R$^2$=H)

By the reaction of alcohol 18B (0.2 mmole) and 3-dimethylaminopropylchloride-hydrochloride (1.9 mmole), dimethyl-(3-[2-(2-trimethylsilyl-ethoxymethyl)-2H-8-oxa-1,2-diaza-dibenzo[e,h]azulene-3-ylmethoxy]-propyl-amine in the form of an oil was obtained.
$^1$H NMR (ppm, CDCl$_3$): 0.06 (s, 9H); 0.92 (m, 2H); 2.07 (m, 2H); 2.57 (m, 2H); 2.89 (m, 2H); 3.67-3.73 (m, 2H); 4.78 (s, 2H); 5.67 (s, 2H); 7.18-7.81 (m, 8H).
MS(m/z): 480.3 [MH]$^+$.
After the removal of N-protecting group and the purification of the product by chromatography on a column, a tautomeric mixture of
dimethyl-[3-(1H-8-oxa-1,2-diaza-dibenzo[e,h]azulene-3-ylmethoxy)-propyl]-amine and
dimethyl-[3-(2H-8-oxa-1,2-diaza-dibenzo[e,h]azulene-3-ylmethoxy)-propyl]-amine in the form of an oil was obtained.
MS(m/z): 350.2 [MH]$^+$.

Example 8 a) Dimethyl-{2-[2-(2-trimethylsilyl-ethoxymethyl)-2H-8-thia-1,2-diaza-dibenzo[e,h]azulene-3-yl-methoxy]-ethyl}-amine (IB; X=S, Y=Z=H, R$^1$=(CH$_3$)$_2$N(CH$_2$)$_2$OCH$_2$)R$^2$=(CH$_3$)$_3$Si(CH$_2$)$_2$OCH$_2$)

Dimethyl-[2-(1H-8-thia-1,2-diaza-dibenzo[e,h]azulene-3-ylmethoxy)-ethyl]-amine (IA; X=S, Y=Z=H, R$^1$=(CH$_3$)$_2$N(CH$_2$)$_2$OCH$_2$, R$^2$=H)

Dimethyl-[2-(2H-8-thia-1,2-diaza-dibenzo[e,h]azulene-3-ylmethoxy)-ethyl]-amine (IB; X=S, Y=Z=H, R$^1$=(CH$_3$)$_2$N(CH$_2$)$_2$OCH$_2$, R$^2$=H)

To a solution of 2-dimethylaminoethylchloride-hydrochloride (2.1 mmole) in 50% sodium hydroxide (2.5 ml), benzyltriethylammonium chloride (50 mg) and a solution of alcohol 19B (0.21 mmole) in toluene (15 ml) were added. The reaction mixture was heated under vigorous stirring at boiling temperature for 4 hours. Then it was cooled to room temperature, diluted with water and extracted with dichloromethane. The organic extract was washed with water, dried over anhydrous Na$_2$SO$_4$ and evaporated under reduced pressure. After purifying the evaporated residue by chromatography on a column,
dimethyl-{2-[2-(2-trimethylsilanyl-ethoxymethyl)-2H-8-thia-1,2-diaza-dibenzo[e,h]azulene-3-ylmethoxy]-ethyl}-amine in the form of an oil was isolated.
MS(m/z): 482.2 [MH]$^+$.
After the removal of N-protecting group and the purification of the product by chromatography on a column as described in Example 7, a tautomeric mixture of
dimethyl-[2-(1H-8-thia-1,2-diaza-dibenzo[e,h]azulene-3-ylmethoxy)-ethyl]-amine and
dimethyl-[2-(2H-8-thia-1,2-diaza-dibenzo[e,h]azulene-3-ylmethoxy)-ethyl]-amine in the form of an oil was obtained.
MS(m/z): 352 [MH]$^+$; 350 [M–H]$^-$ b) Dimethyl-{3-[2-(2-trimethylsilyl-ethoxymethyl)-2H-8-thia-1,2-diaza-dibenzo[e,h]azulene-3-yl-methoxy]-propyl}-amine (IB; X=S, Y=Z=H, R$^1$=(CH$_3$)$_2$N(CH$_2$)$_3$OCH$_2$, R$^2$=(CH$_3$)$_3$Si(CH$_2$)$_2$OCH$_2$)

Dimethyl-[3-(1H-8-thia-1,2-diaza-dibenzo[e,h]azulene-3-ylmethoxy)-propyl]-amine (IA; X=S, Y=Z=H, R$^1$=(CH$_3$)$_2$N(CH$_2$)$_3$OCH$_2$, R$^2$=H)

Dimethyl-[3-(2H-8-thia-1,2-diaza-dibenzo[e,h]azulene-3-ylmethoxy)-propyl]-amine (IB, X=S, Y=Z=H, R$^1$=(CH$_3$)$_2$N(CH$_2$)$_3$OCH$_2$, R$^2$=H)

By the reaction of alcohol 19B (0.15 mmole) and 3-dimethylaminopropylchloride-hydrochloride (1.8 mmole), dimethyl-{3-[2-(2-trimethylsilyl-ethoxymethyl)-2H-8-thia-1,2-diaza-dibenzo[e,h]azulene-3-ylmethoxy]-propyl}-amine in the form of an oily product was obtained.
MS(m/z): 496 [MH]$^+$.
After the removal of N-protecting group and the purification of the product by chromatography on a column as described in Example 7, a tautomeric mixture of
dimethyl-[3-(1H-8-thia-1,2-diaza-dibenzo[e,h]azulene-3-ylmethoxy)-propyl]-amine and
dimethyl-[3-(2H-8-thia-1,2-diaza-dibenzo[e,h]azulene-3-ylmethoxy)-propyl]-amine in the form of an oil was obtained.
MS(m/z): 366 [MH]$^+$; 364 [M–H]$^-$ Example 9 a) {2-[11-Chloro-2-(2-trimethylsilyl-ethoxymethyl)-2H-8-oxa-1,2-diaza-dibenzo[e,h]azulene-3-yl-methoxy]-ethyl}-dimethyl-amine (IB; X=O, Y=H, Z=11-Cl, R$^1$=(CH$_3$)$_2$N(CH$_2$)$_2$OCH$_2$, R$^2$=(CH$_3$)$_3$Si(CH)$_2$OCH$_2$)

[2-(11-Chloro-1H-8-oxa-1,2-diaza-dibenzo[e,h]azulene-3-ylmethoxy)-ethyl]-dimethyl-amine (IA; X=O, Y=H, Z=11-Cl, R$^1$=(CH$_3$)$_2$N(CH$_2$)$_2$OCH$_2$, R$^2$=H)

[2-(11-Chloro-2H-8-oxa-1,2-diaza-dibenzo[e,h]azulene-3-ylmethoxy)-ethyl]-dimethyl-amine (IB; X=O, Y=H$_1$ Z=11-Cl, R$^1$=(CH$_3$)$_2$N(CH$_2$)$_2$OCH$_2$, R$^2$=H)

To a solution of 2-dimethylaminoethylchloride-hydrochloride (2.4 mmole) in 50% sodium hydroxide (5 ml), benzyltriethylammonium chloride (50 mg) and a solution of alcohol 20B (0.23 mmole) in toluene (15 ml) were added. The reaction mixture was heated under vigorous stirring at boiling temperature for 4 hours. Then it was cooled to room temperature, diluted with water and extracted with dichloromethane. The organic extract was washed with water, dried over anhydrous Na$_2$SO$_4$ and evaporated under reduced pressure. After purifying the evaporation residue by chromatography on a column, {2-[11-chloro-2-(2-trimethylsilyl-ethoxymethyl)-2H-8-oxa-1,2-diaza-dibenzo[e,h]azulene-3-ylmethoxy]-ethyl}-dimethyl-amine in the form of an oil was isolated.

MS(m/z): 500.2 [MH]$^+$.

After the removal of N-protecting group and the purification of the product by chromatography on a column, a tautomeric mixture of:

[2-(11-chloro-1H-8-oxa-1,2-diaza-dibenzo[e,h]azulene-3-ylmethoxy)-ethyl]-dimethyl-amine and

[2-(11-chloro-2H-8-oxa-1,2-diaza-dibenzo[e,h]azulene-3-ylmethoxy)-ethyl]-dimethyl-amine in the form of an oil was obtained.

MS(m/z): 370.1 [MH]$^+$.

b) {3-[11-Chloro-2-(2-trimethylsilyl-ethoxymethyl)-2H-8-oxa-1,2-diaza-dibenzo[e,h]azulene-3-yl-methyl]-propyl}-dimethyl-amine (IB; X=O, Y=H, Z=11-Cl, R$^1$=(CH$_3$)$_2$N(CH$_2$)$_3$OCH$_2$, R$^2$=(CH$_3$)$_3$Si(CH$_2$)$_2$OCH$_2$)

[3-(11-Chloro-1H-8-oxa-1,2-diaza-dibenzo[e,h]azulene-3-ylmethoxy)-propyl]-dimethyl-amine (IA; X=O, Y=H, Z=11-Cl, R$^1$=(CH$_3$)$_2$N(CH$_2$)$_3$OCH$_2$, R$^2$=H)

[3-(11-Chloro-2H-8-oxa-1,2-diaza-dibenzo[e,h]azulene-3-ylmethoxy)-propyl]-dimethyl-amine (IB; X=O, Y=H, Z=11-Cl, R$^1$=(CH$_3$)$_2$N(CH$_2$)$_3$OCH$_2$, R$^2$=H)

By the reaction of alcohol 20B (0.23 mmole) and 3-dimethylaminopropylchloride-hydrochloride (2.2 mmole), {3-[11-chloro-2-(2-trimethylsilyl-ethoxymethyl)-2H-8-oxa-1,2-diaza-dibenzo[e,h]azulene-3-ylmethoxy]-propyl}-dimethyl-amine in the form of an oil was obtained.

MS(m/z): 514.2 [MH]$^+$.

After the removal of N-protecting group and the purification of the product by chromatography on a column, a tautomeric mixture of

[3-(11-chloro-1H-8-oxa-1,2-diaza-dibenzo[e,h]azulene-3-ylmethoxy)-propyl]-dimethyl-amine and

[3-(11-chloro-2H-8-oxa-1,2-diaza-dibenzo[e,h]azulene-3-ylmethoxy)-propyl]-dimethyl-amine in the form of an oil was obtained.

MS(m/z): 384.2 [MH]$^+$.

Preparation of the Starting Compounds

Process A 1H-8-Oxa-1,2-diaza-dibenzo[e,h]azulene (1A)

2H-8-Oxa-1,2-diaza-dibenzo[e,h]azulene (1B).

An ethanolic solution of 11-dimethylaminomethylene-11H-dibenzo[b,f]oxepin-10-one (6 mmole) was cooled to 0° C. and to such cooled solution hydrazine hydrate (3 ml) was added. The reaction mixture was stirred at a temperature from 0 to 5° C. for 2 hours, then the solvent was evaporated under reduced pressure and the dry residue was dissolved in a mixture of water and dichloromethane. The crude product obtained after extraction with dichloromethane was purified by chromatography on a silica gel column, whereby a crystalline product of yellow colour was obtained.

According to the above process, starting from the compound 11-dimethylaminomethylene-11H-dibenzo[b,f]oxepin-10-one there was prepared a tautomeric mixture of 1H-8-thia-1,2-diaza-dibenzo[e,h]azulene (2A) and 2H-8-thia-1,2-diaza-dibenzo[e,h]azulene (2B), and starting from the compound 8-chloro-1-dimethylaminomethylene-11H-dibenzo[b,f]oxepin-10-one there was prepared a tautomeric mixture of 11-chloro-1H-8-oxa-1,2-diaza-dibenzo[e,h]azulene (3A) and 11-chloro-2H-8-oxa-1,2-diaza-dibenzo[e,h]azulene (3B).

Process B

2-Phenethyl-2H-8-oxa-1,2-diaza-dibenzo[e,h]azulene (4B)

The tautomeric mixture of compounds 1H-8-oxa-1,2-diaza-dibenzo[e,h]azulene (1A) and 2H-8-oxa-1,2-diaza-dibenzo[e,h]azulene (1B) (3.93 mmole) was dissolved in tethrahydrofuran (10 ml). To the solution sodium hydride (60% dispersion in mineral oil, 200 mg) was slowly added. When hydrogen stopped to develop (approx. 30 minutes), n-tetrabutylammonium iodide (of a catalytic amount) and 2-phenylethyl bromide (8 mmole) were added. Then the reaction mixture was heated at boiling temperature for 5 hours, the solvent was evaporated under reduced pressure and the dry residue was dissolved in a mixture of water and dichloromethane. The organic product was extracted with dichloromethane and the crude product was purified by chromatography on a silica gel column, whereupon a crystalline product of a yellow colour was isolated.

According to the above process starting from the tautomeric mixture 2A and 2B 2-phenethyl-2H-8-thia-1,2-diaza-dibenzo[e,h]azulene (5B) was prepared.

Process C 2-(2-Trimethylsilyl-ethoxymethyl)-2H-8-oxa-1,2-diaza-dibenzo[e,h]azulene (6B)

The tautomeric mixture of the compounds 1H-8-oxa-1,2-diaza-dibenzo[e,h]azulene (1A) and 2H-8-oxa-1,2-diaza-dibenzo[e,h]azulene (1B) (5.1 mmole) was dissolved in tetrahydrofuran (25 ml). To the solution sodium hydride (60% dispersion in mineral oil, 475 mg) was slowly added. When hydrogen stopped to develop (approx. 30 minutes), 2-chloromethoxyethyl-trimethyl silane (5.7 mmole) was added and the reaction mixture was heated at boiling temperature for 5 hours, the solvent was evaporated under reduced pressure and the dry residue was dissolved in a mixture of water and dichloromethane. The organic product was extracted with dichloromethane and the crude product was purified by chromatography on a silica gel column, whereupon a crystalline product of yellow colour was isolated.

Starting from the tautomeric mixture of 2A and 2B, the isomer 2-(2-trimethylsilyl-ethoxymethyl)-2H-8-thia-1,2-diaza-dibenzo[e,h]azulene (7B) was prepared.

Starting from the tautomeric mixture of 3A and 3B, the isomer 11-chloro-2-(2-trimethylsilyl-ethoxymethyl)-2H-8-oxa-1,2-diaza-dibenzo[e,h]azulene (8B) was prepared.

Process D

2-Phenethyl-2H-8-oxa-1,2-diaza-dibenzo[e,h]azulene-3-carbaldehyde (9B)

Compound 4B (1.5 mmole), in a stream of argon, was dissolved in dry THF (15 ml) and the solution was cooled to −78° C. To the solution n-BuLi (1M solution in THF, 3.6 mmole) was added dropwise. The reaction mixture was stirred at −78° C. for 60 minutes and then dimethyl formamide (1 ml) was added. Then the reaction mixture was gradually heated to room temperature, at which it was stirred for 30 minutes. Then a small amount of water (1 ml) was added to the reaction mixture and the organic product was extracted with dichloromethane. The crude product was purified by chromatography on a silica gel column, whereupon an oily product was isolated.

According to the above process by the formylation of the compounds 5B, 6B, 7B, 8B, there were prepared compounds:
2-phenethyl-2H-8-thia-1,2-diaza-dibenzo[e,h]azulene-3-carbaldehyde (10B),
2-(2-trimethylsilyl-ethoxymethyl)-2H-8-oxa-1,2-diaza-dibenzo[e,h]azulene-3-carbaldehyde (11B),
2-(2-trimethylsilyl-ethoxymethyl)-2H-8-thia-1,2-diaza-dibenzo[e,h]azulene-3-carbaldehyde (12B),
11-chloro-2-(2-trimethylsilyl-ethoxymethyl)-2H-8-oxa-1,2-diaza-dibenzo[e,h]azulene-3-carbaldehyde (13B).

TABLE 2

Starting compounds and intermediates of the formula I

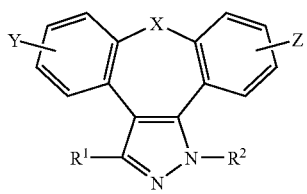

IA

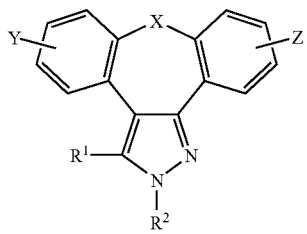

IB

| Comp. | X | Y | Z | $R^1$ | $R^2$ | MS(m/z) | $^1$H NMR(ppm) |
|---|---|---|---|---|---|---|---|
| 1A<br>1B | O | H | H | H | H | 235[MH]$^+$ | 7.14-7.39(m, 6H); 7.43(d, 1H); 7.70(d, 1H); 7.89(s, 1H); 9.09(bs, 1H) |
| 2A<br>2B | S | H | H | H | H | 251[MH]$^+$ | 6.51(bs, 1H); 7.27-7.74(m, 8H); 7.94(d, 1H) |
| 3A<br>3B | O | H | 11-Cl | H | H | 269[MH]$^+$ | 7.18-7.54(m, 6H); 7.80(d, 1H); 8.06(s, 1H); 9.1(bs, 1H) |
| 4B | O | H | H | H | Ph(CH$_2$)$_2$ | 339[MH]$^+$ | 3.25(t, 2H); 4.44(t, 2H); 7.08-7.41(m, 13H); 7.88(d, 1H) |
| 5B | S | H | H | H | Ph(CH$_2$)$_2$ | 355[MH]$^+$ | 3.31(t, 2H); 4.5(t, 2H); 7.14-7.88(m, 13H); 7.88(d, 1H) |
| 6B | O | H | H | H | SEM$^a$ | 387 [M + Na$^+$] | 0.04(s, 9H); 0.94-0.99(m, 2H); 3.70(t, 2H); 5.59(s, 2H); 7.14-8.01(m, 9H) |
| 7B | S | H | H | H | SEM | 402.9 [M + Na$^+$] | 0.01(s, 9H); 0.92-1.02(m, 2H); 3.68-3.79(m, 2H); 5.49-5.54(m, 2H); 7.19-7.90(m, 9H) |
| 8B | O | H | 11-Cl | H | SEM | 420.8 [M + Na$^+$] | 0.03(s, 9H); 0.94-1.07(m, 2H); 3.69(m, 2H); 5.6(s, 2H); 7.15-8.04(m, 8H) |
| 9B | O | H | H | CHO | Ph(CH$_2$)$_2$ | 367.3 [MH]$^+$ | 3.21(t, 2H); 4.9(m, 2H); 7.21-7.84(m, 13H); 10.0(s, 1H) |
| 10B | S | H | H | CHO | Ph(CH$_2$)$_2$ | 383[MH]$^+$ | 3.24(m, 2H); 4.92(t, 2H); 7.08-7.81(m, 13H); 9.80(d, 1H) |
| 11B | O | H | H | CHO | SEM | 415.2 [M + Na$^+$] | 0.03(s, 9H); 0.89-1.05(m, 2H); 3.73(t, 2H); 5.96(s, 2H); 7.24-7.9(m, 7H); 8.0(dd, 1H); 10.12(s, 1H) |
| 12B | S | H | H | CHO | SEM | 431.1 [M + Na$^+$] | 0.03(s, 9H); 0.89-1.03(m, 2H); 3.73-3.84(m, 2H); 5.99(s, 2H); 7.28-7.94(m, 8H); 10.19(s, 1H) |
| 13B | O | H | 11-Cl | CHO | SEM | 448.9 [M + Na$^+$] | 0.07(s, 9H); 0.93(m, 2H); 3.69(t, 2H); 5.92(s, 2H); 7.3-7.58(m, 7H); 10.15(d, 1H) |

$^a$SEM = (CH$_3$)$_3$SiCH$_2$CH$_2$OCH$_2$

The invention claimed is:
1. A compound of the formula I

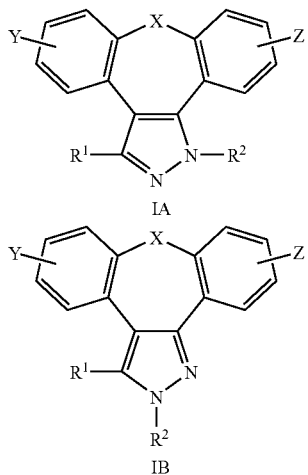

wherein
X is $CH_2$ or a hetero atom selected from O, S, S(=O), $S(=O)_2$, and $NR^a$, wherein $R^a$ is hydrogen or a protecting group;
Y and Z independently from each other denote one or more identical or different substituents linked to any available carbon atom, selected from H, halogen, $C_1$-$C_4$ alkyl, $C_2$-$C_4$ alkenyl, $C_2$-$C_4$ alkinyl, halo-$C_1$-$C_4$ alkyl, hydroxy, $C_1$-$C_4$ alkoxy, trifluoromethoxy, $C_1$-$C_4$ alkanoyl, amino, amino-$C_1$-$C_4$ alkyl, N—($C_1$-$C_4$-alkyl) amino, N,N-di($C_1$-$C_4$-alkyl)amino, thiol, $C_1$-$C_4$ alkylthio, sulfonyl, $C_1$-$C_4$ alkylsulfonyl, sulfinyl, $C_1$-$C_4$ alkylsulfinyl, carboxy, $C_1$-$C_4$ alkoxycarbonyl, cyano, and nitro;
$R^1$ is H, halogen, an optionally substituted heteroaryl or heterocycle, hydroxy, $C_1$-$C_7$ alkoxy, aryloxy, amino, N—($C_1$-$C_7$)alkylamino, N,N-di($C_1$-$C_7$-alkyl)amino, ($C_1$-$C_7$-alkyl)amino, amino-$C_1$-$C_7$ alkoxy, $C_1$-$C_7$ alkanoyl, aroyl, $C_1$-$C_7$ alkanoyloxy, carboxy, an optionally substituted $C_1$-$C_7$ alkyloxycarbonyl or aryloxycarbonyl, carbamoyl, N—($C_1$-$C_7$-alkyl)carbamoyl, N,N-di($C_1$-$C_7$-alkyl)carbamoyl, cyano, nitro,
or a substituent of the formula II:

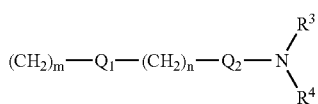

wherein
$R^3$ and $R^4$ simultaneously or independently from each other are selected from hydrogen, $C_1$-$C_4$ alkyl, aryl or together with N have the meaning of an optionally substituted heterocycle and heteroaryl;
m and n represent an integer from 0 to 3;
$Q_1$ and $Q_2$ represent, independently from each other, oxygen, sulfur or groups

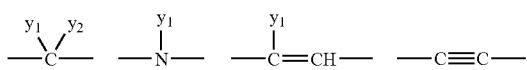

wherein the substituents
$Y_1$ and $Y_2$ independently from each other are selected from hydrogen, halogen, an optionally substituted $C_1$-$C_4$ alkyl or aryl, hydroxy, $C_1$-$C_4$ alkoxy, $C_1$-$C_4$ alkanoyl, thiol, $C_1$-$C_4$ alkylthio, sulfonyl, $C_1$-$C_4$ alkylsulfonyl, sulfinyl, $C_1$-$C_4$ alkylsulfinyl, cyano, nitro or together form carbonyl and imino group;
$R^2$ has the meaning of hydrogen, optionally substituted $C_1$-$C_7$ alkyl or aryl or a protecting group: formyl, $C_1$-$C_7$ alkanoyl, $C_1$-$C_7$ alkoxycarbonyl, arylalkyloxycarbonyl, aroyl, arylalkyl, $C_1$-$C_7$ alkylsilyl; or
Dimethyl-{2-[2-(8-thia-1,2-diaza-dibenzo[e,h]azulene-1-yl)-ethoxy]-ethyl}-amine;
Dimethyl-{3-[2-(8-thia-1,2-diaza-dibenzo[e,h]azulene-1-yl)-ethoxy]-propyl}-amine;
Dimethyl-{2-[2-(8-thia-1,2-diaza-dibenzo[e,h]azulene-2-yl)-ethoxy]-ethyl}-amine;
Dimethyl-{3-[2-(8-thia-1,2-diaza-dibenzo[e,h]azulene-2-yl)-ethoxy]-propyl}-amine;
as well as pharmacologically acceptable salts thereof.
2. The compound according to claim 1, wherein X has the meaning of S or O.
3. The compound according to claim 2, wherein Y has the meaning of H and Z has the meaning of H or Cl.
4. The compound according to claim 3, wherein $R^1$ has the meaning of CHO or $CH_2OH$ and $R^2$ has the meaning of H, $(CH_3)_3SiCH_2CH_2OCH_2$ or $C_6H_5CH_2CH_2$.
5. The compound according to claim 3, wherein $R^1$ has the meaning of formula II.
6. The compound according to claim 5, wherein symbol m has the meaning of 1, $Q_1$ has the meaning of O, n has the meaning of 1 or 2, $Q_2$ has the meaning of $CH_2$, $R^2$ has the meaning of H, $(CH_3)_3SiCH_2CH_2OCH_2$ or $C_6H_5CH_2CH_2$ and $R^3$ and $R^4$ have the meaning of H or $CH_3$.
7. The compound of claim 4 selected from the group consisting of:
2-(8-Oxa-1,2-diaza-dibenzo[e,h]azulene-1-yl)-ethanol;
2-(8-Oxa-1,2-diaza-dibenzo[e,h]azulene-2-yl)-ethanol;
2-(8-Thia-1,2-diaza-dibenzo[e,h]azulene-1-yl)-ethanol;
2-(8-Thia-1,2-diaza-dibenzo[e,h]azulene-2-yl)-ethanol;
(2-Phenethyl-2H-8-oxa-1,2-diaza-dibenzo[e,h]azulene-3-yl)-methanol;
(2-Phenethyl-2H-8-thia-1,2-diaza-dibenzo[e,h]azulene-3-yl)-methanol;
[2-(2-Trimethylsilyl-ethoxymethyl)-2H-8-oxa-1,2-diaza-dibenzo[e,h]azulene-3-yl]-methanol;
[2-(2-Trimethylsilyl-ethoxymethyl)-2H-8-thia-1,2-diaza-dibenzo[e,h]azulene-3-yl]-methanol;
[11-Chloro-2-(2-trimethylsilyl-ethoxymethyl)-2H-8-oxa-1,2-diaza-dibenzo[e,h]azulene-3-yl]-methanol,
and pharmacologically acceptable salts thereof.
8. The compound and salt of claim 6 selected from the group consisting of:
Dimethyl-{2-[2-(8-thia-1,2-diaza-dibenzo[e,h]azulene-1-yl)-ethoxy]-ethyl}-amine;
Dimethyl-{3-[2-(8-thia-1,2-diaza-dibenzo[e,h]azulene-1-yl)-ethoxy]-propyl}-amine;
Dimethyl-{2-[2-(8-thia-1,2-diaza-dibenzo[e,h]azulene-2-yl)-ethoxy]-ethyl}-amine;
Dimethyl-{3-[2-(8-thia-1,2-diaza-dibenzo[e,h]azulene-2-yl)-ethoxy]-propyl}-amine;
Dimethyl-[2-(2-phenethyl-2H-8-oxa-1,2-diaza-dibenzo[e,h]azulene-3-ylmethoxy)-ethyl]-amine;
Dimethyl-[3-(2-phenethyl-2H-8-oxa-1,2-diaza-dibenzo[e,h]azulene-3-ylmethoxy)-propyl]-amine;
Dimethyl-[2-(2-phenethyl-2H-8-thia-1,2-diaza-dibenzo[e,h]azulene-3-ylmethoxy)-ethyl]-amine;
Dimethyl-[3-(2-phenethyl-2H-8-thia-1,2-diaza-dibenzo[e,h]azulene-3-ylmethoxy)-propyl]-amine, Dimethyl-{2-[2-(2-trimethylsilyl-ethoxymethyl)-2H-8-oxa-1,2-diaza-dibenzo[e,h]azulene-3-ylmethoxy]-ethyl}-amine;
Dimethyl-[2-(1H-8-oxa-1,2-diaza-dibenzo[e,h]azulene-3-ylmethoxy)-ethyl]-amine;
Dimethyl-[2-(2H-8-oxa-1,2-diaza-dibenzo[e,h]azulene-3-ylmethoxy)-ethyl]-amine;
Dimethyl-{3-[2-(2-trimethylsilyl-ethoxymethyl)-2H-8-oxa-1,2-diaza-dibenzo[e,h]azulene-3-ylmethoxy]-propyl}-amine;
Dimethyl-[3-(1H-8-oxa-1,2-diaza-dibenzo[e,h]azulene-3-ylmethoxy)-propyl]-amine;
Dimethyl-[3-(2H-8-oxa-1,2-diaza-dibenzo[e,h]azulene-3-ylmethoxy)-propyl]-amine;
Dimethyl-{2-[2-(2-trimethylsilyl-ethoxymethyl)-2H-8-thia-1,2-diaza-dibenzo[e,h]azulene-3-ylmethoxy]-ethyl}-amine;
Dimethyl-[2-(1H-8-thia-1,2-diaza-dibenzo[e,h]azulene-3-ylmethoxy)-ethyl]-amine;
Dimethyl-[2-(2H-8-thia-1,2-diaza-dibenzo[e,h]azulene-3-ylmethoxy)-ethyl]-amine;
Dimethyl-{3-[2-(2-trimethylsilyl-ethoxymethyl)-2H-8-thia-1,2-diaza-dibenzo[e,h]azulene-3-ylmethoxy]-propyl}-amine;
Dimethyl-[3-(1H-8-thia-1,2-diaza-dibenzo[e,h]azulene-3-ylmethoxy)-propyl]-amine;
Dimethyl-[3-(2H-8-thia-1,2-diaza-dibenzo[e,h]azulene-3-ylmethoxy)-propyl]-amine;
{2[11-Chloro-2-(2-trimethylsilyl-ethoxymethyl)-2H-8-oxa-1,2-diaza-dibenzo[e,h]azulene-3-ylmethoxy]-ethyl}-dimethyl-amine;
[2-(11-Chloro-1H-8-oxa-1,2-diaza-dibenzo[e,h]azulene-3-ylmethoxy)-ethyl]-dimethyl-amine;
[2-(11-Chloro-2H-8-oxa-1,2-diaza-dibenzo[e,h]azulene-3-ylmethoxy)-ethyl]-dimethyl-amine;
{3-[11-Chloro-2-(2-trimethylsilyl-ethoxymethyl)-2H-8-oxa-1,2-diaza-dibenzo[e,h]azulene-3-ylmethoxy]-propyl}-dimethyl-amine,
[3-(11-Chloro-1H-8-oxa-1,2-diaza-dibenzo[e,h]azulene-3-ylmethoxy)-propyl]-dimethyl-amine; and
[3-(11-Chloro-2H-8-oxa-1,2-diaza-dibenzo[e,h]azulene-3-ylmethoxy)-propyl]-dimethyl-amine.

9. A process for the preparation of compounds of the formula I:

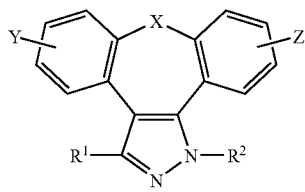

IA

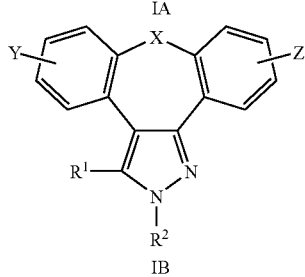

IB wherein

X is $CH_2$ or a hetero atom selected from O, S, S(=O), S(=O)$_2$, and NR$^a$, wherein R$^a$ is hydrogen or a protecting group;

Y and Z independently from each other denote one or more identical or different substituents linked to any available carbon atom, selected from H, halogen, $C_1$-$C_4$ alkyl, $C_2$-$C_4$ alkenyl, $C_2$-$C_4$ alkinyl, halo-$C_1$-$C_4$ alkyl, hydroxy, $C_1$-$C_4$ alkoxy, trifluoromethoxy, $C_1$-$C_4$ alkanoyl, amino, amino-$C_1$-$C_4$ alkyl, N—($C_1$-$C_4$-alkyl)amino, N,N-di($C_1$-$C_4$-alkyl)amino, thiol, $C_1$-$C_4$ alkylthio, sulfonyl, $C_1$-$C_4$ alkylsulfonyl, sulfinyl, $C_1$-$C_4$ alkylsulfinyl, carboxy, $C_1$-$C_4$ alkoxycarbonyl, cyano, and nitro;

$R^1$ is H, halogen, an optionally substituted heteroaryl or heterocycle, hydroxy, $C_1$-$C_7$ alkoxy, aryloxy, amino, N—($C_1$-$C_7$)alkylamino, N,N-di($C_1$-$C_7$-alkyl)amino, ($C_1$-$C_7$-alkyl)amino, amino-$C_1$-$C_7$ alkoxy, $C_1$-$C_7$-, alkanoyl, aroyl, $C_1$-$C_7$ alkanoyloxy, carboxy, an optionally substituted $C_1$-$C_7$ alkyloxycarbonyl or aryloxycarbonyl, carbamoyl, N—($C_1$-$C_7$-alkyl)carbamoyl, N,N-di($C_1$-$C_7$-alkyl)carbamoyl, cyano, nitro, or a substituent of the formula II:

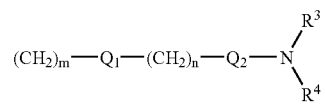

wherein $R^3$ and $R^4$ simultaneously or independently from each other are selected from hydrogen, $C_1$-$C_4$ alkyl, aryl or together with N have the meaning of an optionally substituted heterocycle and heteroaryl;

m and n represent an integer from 0 to 3;

$Q_1$ and $Q_2$ represent, independently from each other, oxygen, sulfur or groups

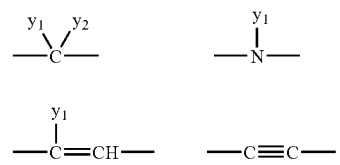

wherein the substituents $y_1$ and $y_2$ independently from each other are selected from hydrogen, halogen, an optionally substituted $C_1$-$C_4$ alkyl or aryl, hydroxy, $C_1$-$C_4$ alkoxy, $C_1$-$C_4$ alkanoyl, thiol, $C_1$-$C_4$ alkylthio, sulfonyl, $C_1$-$C_4$ alkylsulfonyl, sulfinyl, $C_1$-$C_4$ alkylsulfinyl, cyano, nitro or together form carbonyl and imino group;

$R^2$ has the meaning of hydrogen, optionally substituted $C_1$-$C_7$ alkyl or aryl or a protecting group: formyl, $C_1$-$C_7$ alkanoyl, $C_1$-$C_7$ alkoxycarbonyl, arylalkyloxycarbonyl, aroyl, arylalkyl, $C_1$-$C_7$ alkylsilyl;

as well as pharmacologically acceptable salts thereof, characterized in that the preparation processes comprise a) for the compounds of the formula I, wherein $R^1$ has the meaning of CHO, formylation of the compounds of the formula III

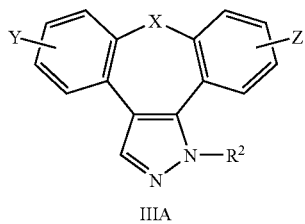

IIIA

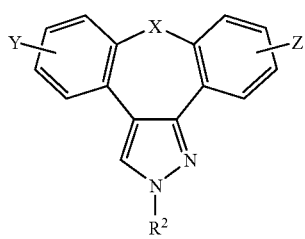

IIIB b) for the compounds of the formula I, wherein $Q_1$ has the meaning —O—, a reaction of alcohols of the formula IV

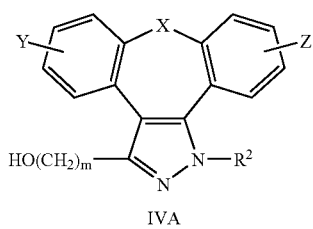

IVA

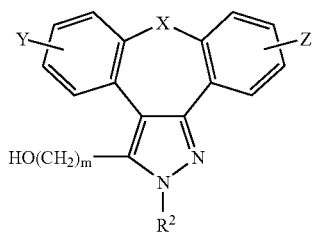

IVB with compounds of the formula V

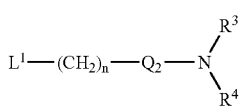

V wherein $L^1$ has the meaning of a leaving group, c) for the compounds of the formula I, wherein $Q_1$ has the meaning of —O—, —NH—, —S— or —C≡C—, a reaction of the compounds of the formula VI

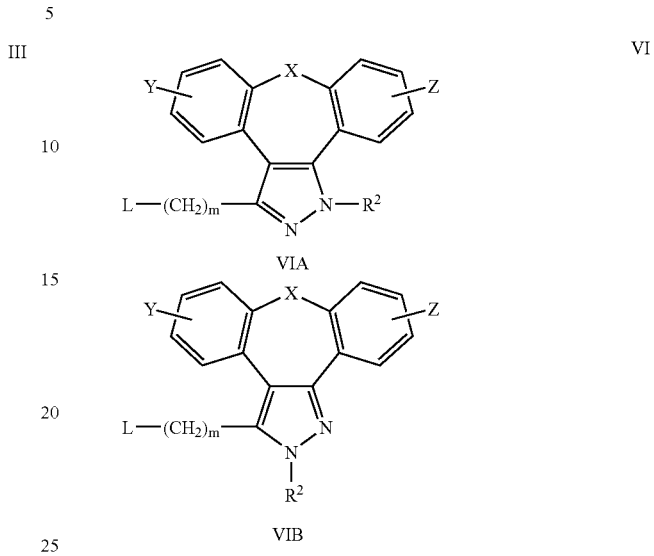

wherein L has the meaning of a leaving group, with compounds of the formula VII

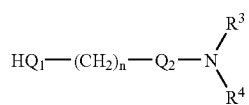

VII d) for the compounds of the formula I, wherein $Q_1$ has a meaning of —O—, —NH— or —S—, a reaction of compounds of the formula VIII

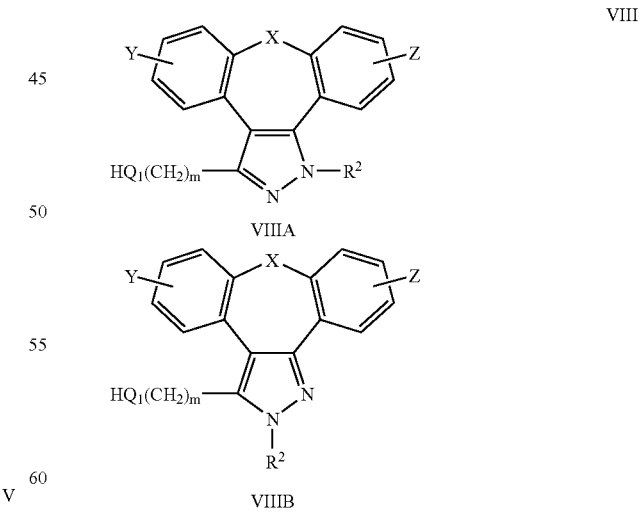

with compounds of the formula V, wherein $L^1$ has the meaning of a leaving group e) for the compounds of the formula I, wherein $Q_1$ has the meaning of —C≡C—, a reaction of the compounds of the formula VIII, wherein $Q_1$ has the meaning of carbonyl, with phosphorous ylides.

10. A method of treating inflammation associated with TNF-α comprising administering to a subject in need thereof a compound according to claim 5.

11. The method of claim 10, wherein the inflammation associated with TNF-α is inflammation associated with rheumatoid arthritis.

* * * * *